United States Patent [19]
Imbach et al.

[11] Patent Number: 6,124,445
[45] Date of Patent: Sep. 26, 2000

[54] PHOSPHOTRIESTER OLIGONUCLEOTIDES, AMIDITIES AND METHOD OF PREPARATION

[75] Inventors: Jean-Louis Imbach; Gilles Gosselin, both of Montpellier; Bernard Rayner, Barbeyvargues, all of France; Muthiah Manoharan, Carlsbad, Calif.

[73] Assignee: Isis Pharmaceuticals, Inc., Carlsbad, Calif.

[21] Appl. No.: 09/004,940

[22] Filed: Jan. 9, 1998

Related U.S. Application Data

[63] Continuation of application No. 08/816,570, Mar. 12, 1997, Pat. No. 5,955,591, which is a continuation-in-part of application No. 08/777,423, Dec. 30, 1996, abandoned, which is a continuation of application No. 08/658,509, Jun. 10, 1996, abandoned, which is a continuation-in-part of application No. 08/545,785, Jan. 17, 1996, Pat. No. 5,770,713, and a continuation-in-part of application No. 08/343,433, Nov. 23, 1994, abandoned.

[51] Int. Cl.$^7$ .......................... C07H 19/06; C07H 19/16; C07H 21/00
[52] U.S. Cl. ................. 536/23.1; 536/22.1; 536/25.3; 536/25.31; 536/25.32; 536/25.33; 536/25.34; 536/26.71; 536/26.72; 536/26.74; 536/26.8
[58] Field of Search .................... 536/25.3, 25.31, 536/25.32, 25.33, 25.34, 22.1, 23.1, 26.7, 26.71, 26.72, 26.74, 26.8

[56] References Cited

U.S. PATENT DOCUMENTS

| | | |
|---|---|---|
| Re. 34,069 | 9/1992 | Koster et al. . |
| 3,687,808 | 8/1972 | Merigan et al. . |
| 4,415,732 | 11/1983 | Caruthers et al. . |
| 4,458,066 | 7/1984 | Caruthers et al. . |
| 4,469,863 | 9/1984 | Ts'o et al. . |
| 4,500,707 | 2/1985 | Caruthers et al. . |
| 4,511,713 | 4/1985 | Miller et al. . |
| 4,517,338 | 5/1985 | Urdea et al. . |
| 4,659,774 | 4/1987 | Webb et al. . |
| 4,668,777 | 5/1987 | Caruthers et al. . |
| 4,672,110 | 6/1987 | Letsinger . |
| 4,725,677 | 2/1988 | Koster et al. . |
| 4,973,679 | 11/1990 | Caruthers et al. . |
| 5,000,307 | 3/1991 | Bruke . |
| 5,132,418 | 7/1992 | Caruthers et al. . |
| 5,153,319 | 10/1992 | Caruthers et al. . |
| 5,210,264 | 5/1993 | Yau . |
| 5,218,103 | 6/1993 | Caruthers et al. . |
| 5,268,464 | 12/1993 | Brill . |
| 5,278,302 | 1/1994 | Caruthers et al. . |
| 5,292,875 | 3/1994 | Stec et al. . |
| 5,319,079 | 6/1994 | Reddy et al. . |
| 5,430,136 | 7/1995 | Urdea et al. . |
| 5,430,138 | 7/1995 | Urdea et al. . |
| 5,466,786 | 11/1995 | Buhr et al. . |
| 5,529,150 | 6/1996 | Wyrzykiewicz . |
| 5,536,821 | 7/1996 | Agrawal et al . |
| 5,541,306 | 7/1996 | Agrawal et al. . |
| 5,606,049 | 2/1997 | Vaghefi . |
| 5,623,065 | 4/1997 | Cook et al. . |
| 5,644,048 | 7/1997 | Yau . |
| 5,646,267 | 7/1997 | Stec et al. . |

FOREIGN PATENT DOCUMENTS

| | | |
|---|---|---|
| 0 217 580 | 4/1987 | European Pat. Off. . |
| 0 322 384 | 6/1989 | European Pat. Off. . |
| 0 481 214 | 9/1991 | European Pat. Off. . |
| 0463712 | 1/1992 | European Pat. Off. . |
| 0519463 | 12/1992 | European Pat. Off. . |
| 0 649 855 A1 | 4/1995 | European Pat. Off. . |
| 2 654 106 | 10/1991 | France . |
| WO 88/00201 | 1/1988 | WIPO . |
| WO 90/08155 | 7/1990 | WIPO . |
| WO 91/04983 | 4/1991 | WIPO . |
| WO 91/14696 | 10/1991 | WIPO . |
| WO 91/17169 | 11/1991 | WIPO . |
| WO 91/19721 | 12/1991 | WIPO . |
| WO 94/02501 | 2/1994 | WIPO . |

OTHER PUBLICATIONS

Hao, Z. et al., "Potent DNA Chain Termination Activity and Selective Inhibition of Human Immunodeficiency Virus Reverse Transcriptase by 2', 3'–Dideoxyuridine–5'–triphosphate", *Molecular Pharmacology*, 1990, 37, 157–163.

Hao, Z. et al, "2',3'–Dideoxyuridine Triphosphate: A Potent Inhibitor of HIV Reverse Transcriptase", *Proceedings of AACR*, 1988, 29, 348.

Matthes, E. et al., "Inhibition of HIV–Associated Reverse Transcriptase By Sugar–Modified Derivatives of Thymidine 5'–Triphosphate in Comparison to Cellular DNA Polymerases α and β", *Biochem. Biophys. Res. Commun.*, 1987, 148(1), 78–85.

Rosenberg et al., "Synthesis of Potential Prodrugs and Metabolites of 9–(S)–3–Hydroxy–2–Phosphonylmethoxypropyl)Adenine", *Coll. Czech. Chem. Comm.*, 1987, 52, 2792–2800.

Marshall et al., "Phosphorodithioate DNA as a Potential Therapeutic Drug", *Science*, 1993, 259, 1564–1570.

Alul, R.H. et al., "Oxalyl–CPG: a labile support for synthesis of sensitive oligonucleotide derivatives", *Nucl. Acids Res.*, 1991, 19(7), 1527–1532.

Barber, I. et al., "The Prooligonucleotide Approach: II. Synthesis and Stability Studies of Chimeric Oligonucleotide Models", *Bioorg. Med. Chem. Lett.*, 1995, 5, 1441–1444.

Beaucage et al., "Deoxynucleoside Phosphoramidites—A New Class of Key Intermidiates for Deoxypolynucleotide Synthesis", *Tetra. Lett.*, 1981, 22, 1859–1862.

(List continued on next page.)

*Primary Examiner*—James O. Wilson
*Attorney, Agent, or Firm*—Woodcock Washburn Kurtz Mackiewicz & Norris LLP

[57] ABSTRACT

Oligonucleotides having bioreversible phosphate blocking groups can be used as pro drugs for the oligonucleotides. The bio-reversible blocking groups can be removed by intercellular enzymes, particularly carboxyesterases, to provide the unprotected oligonucleotide. The oligonucleotides can be prepared via post synthesis alkylation reactions or utilizing amidite type chemistry wherein the bioreversible phosphorus protecting group is formed as an integral part of the amidite reagent.

62 Claims, 6 Drawing Sheets

OTHER PUBLICATIONS

Beaucage et al., "Advance in the Synthesis of Oligonucleotides by the Phophoramidite Approach", *Tetrahedron,* 1992, 48(12), 2223–2311.

Beaucage et al., "The Synthesis of Modified Oligonucleotides by the Phophoramidite Approach and Their Applications", *Tetrahedron,* 1993, 49(28), 6123–6194.

Caruthers, *Oligonucleotides: Antisense Inhibitors of Gene Expression,* pp. 7–24, J. S. Cohen (ed.), CRC Press, Inc. Boca Raton, Florida, 1989.

*Concise Encyclopedia Of Polymer Science And Engineering,* pp. 858–859, Kroschwitz, J.I., ed. John Wiley & Sons, 1990.

Crooke et al., "Progress In Antisense Oligonucleotide Therapeutics", *Annu. Rev. Pharmacol. Toxicol.,* 1996, 36, 107–129.

Crooke, S.T., *Nucleic Acid Therapeutics In Pharmaceutical Manufacturing International,* Sterling, London, 89, 1992.

Englisch et al., "Chemically Modified Oligonucleotides as Probes and Inhibitors", *Angewandte Chemie, International Edition,* 1991, 30(6), 613–629.

Iyer et al., "3H–1,2–Benzodithiole–3–one 1,1–Dioxide as an Improved Sulfurizing Reagent in the Solid–Phase Synthesis of Oligodeoxyribonucleoside Phophorthiates", *J. Am. Chem. Soc.,* 1990, 112, 1253–1254.

Kawasaki et al., "Synthesis and Biophysical Studies of 2'–dRIBO–F Modified Oligonucleotides", Conference On Nucleic Acid Therapeutics, Clearwater, FL, Jan. 13, 1991.

Lefebvre et al., "Mononucleoside Phosphotriester Derivatives with S–Acyl–2–thioethyl Biorevesible Phosphate–Protecting Groups: Intracellular Delivery of 3'–Azido–2', 3'–dideoxythymidine 5'–Monophosphate", *J. Med. Chem.,* 1995, 38, 3941–3950.

Martin, "A New Access to 2'–O–Alkylated Ribonucleosides and Properties of 2'–O–Alkylated Oligoribonucleotides", *Helv. Chim. Acta,* 1995, 78, 486–504 (English abstract).

*Oligonucleotide synthesis, a practical approach,* M.J. Gait (ed.), IRL Press, 1984.

*Oligonucleotides and Analogues, A Practical Approach,* Ed. F. Eckstein, IRL Press, 1991.

Milligan, J.F. et al., "Current Concepts in Antisense Drug Design", *J. Med. Chem.,* 1991, 36(14), 1923–1937.

Pompon, A. et al., "On–Line Internal Surface Reversed–Phase Cleaning: The Direct HPLC Analysis of Crude Biological Samples", *Biochem Pharmacol.,* 1992, 43(8), 1769–1775.

Spiller et al., "The uptake kinetics of chimeric oligodeoxynucleotide analogues in human leukaemia MOLT–4 cells", *Anti–Cancer Drug Design,* 1991, 7, 115–129.

Uhlmann, E. et al., "Antisense Oligonucleotides: A New Therapeutic Principle", *Chem. Rev.,* 1990, 90(4), 544–584.

Varma, R.S., "Synthesis of Oligonucleotide Analogues with Modified Backbones", *Synlett,* 1991, 621–637.

Wiesler et al., "Synthesis and Purification of Phosphorodithioate DNA", Methods in Molecular Biology: Protocols for Nucleotides and Analogs, S. Agrawal (ed.), Humana Press Inc., Totowa, NJ, 1993, 20, 191–206.

Zhao, Q. et al., "Enantioselective and Reversible Inhibition of Trypsin and α–Chymotrypsin by Phophonate Esters", *Biochemistry,* 1994, 33, 8128–8138.

Heikkila, J. et al., "The 2–Nitrophenylsulfenyl (Nps) Group for the Protection of Amino Functions of Cytidine, Adenosine, Guanosine and Their 2'–Deoxysugar Derivatives", *Acta Chemica Scand. B,* 1983, 37, 857–864.

Greene and Wuts, Protective Groups in Organic Synthesis, 2d edition, John Wiley & Sons, New York, 1991.

Ordoukhanian et al., "Design and Synthesis of a Versatile Photocleavable DNA Building Block. Application to Phototriggered Hybridization", *J. Am. Chem. Soc.,* 1995, 117, 9570–9571.

Wright et al., "Large Scale Synthesis of Oligonucleotides via Phosphoramidite Nucleosides and a High–loaded Polystyrene Support", *Tetra. Lett.,* 1993, 34(21), 3373–3376.

PCT International Search Report dated Oct. 17, 1997, 2 pages.

Clivio et al., "Synthesis and Purification of Oligonucleotides Containing Sulfur Substituted Nucleobases: 4–Thiouracil, 4–Thiothymine and 6–Mercaptopurine", *Tetra. Lett.,* 1992, 33(1), 65–68.

Hau et al., "Octathymidylates Involving Alternating Neopentylphosphothionotriester–Phosphodiester Linkages with Controlled Stereochemistry at the Modified P–Center", *Tetra. Lett.,* 1991, 32(22), 2497–2498.

Rosemeyer et al., "1–(2'–Deoxy–β–D–xylofuranosyl)thymine Building Blocks for Solid–Phase Synthesis and Properties of Oligo(2'–Deoxyxylonucleotides)", *Helv. Chim. Acta,* 1991, 74, 748–760.

Sakatsume et al., "Solid Phase Synthesis of Oligoribonucleotides by the Phosphoramidite Approach Using 2'–O–1–(2–Chloroethyoxy)Ethyl Protection", *Tetrahedron,* 1991, 47(41), 8717–8728.

1
2

3
4

PHOSPHOTRIESTER OLIGONUCLEOTIDES, AMIDITIES AND METHOD OF PREPARATION

CROSS REFERENCE TO RELATED APPLICATIONS

This patent application is a continuation of application Ser. No. 08/816,570, filed on Mar. 12, 1997, now U.S. Pat. No. 5,955,591 which is a continuation-in-part of application Ser. No. 08/777,423, filed on Dec. 30, 1996, now abandoned, which is a continuation of application Ser. No. 08/658,509, filed on Jun. 10, 1996, which is now abandoned, in turn, is a continuation-in-part of application Ser. No. 08/545,785, filed on Jan. 17, 1996 (issued as U.S. Pat. No. 5,770,713, Jun. 23, 1998) and application Ser. No. 08/343,433, filed on Nov. 23, 1994 (now abandoned). The foregoing patent applications are incorporated herein by reference.

FIELD OF THE INVENTION

This invention is directed to the synthesis and use of protected forms of oligonucleotides wherein at least one of the phosphate moieties of the oligonucleotide is protected with a protecting group that is removable by intracellular enzymes. Further the invention is directed to amidite reagents for preparing these oligonucleotides. Additionally included in the invention are prodrug forms of oligonucleotides and chimeric oligonucleotides that are modified with certain functional groups that are cleavable by intercellular enzymes to release the oligonucleotide from its prodrug form. The oligonucleotides of the invention can be prepared so as to be of any known sequences that is complementary to a target strand of a mRNA. The compounds of the invention are useful for therapeutics, diagnostics and as research reagents.

BACKGROUND OF THE INVENTION

Oligonucleotides are known to hybridize to single-stranded DNA or RNA molecules. Hybridization is the sequence-specific base pair hydrogen bonding of nucleobases of the oligonucleotides to nucleobases of target DNA or RNA. Such nucleobase pairs are said to be complementary to one another.

The complementarity of oligonucleotides has been used for inhibition of a number of cellular targets. Such complementary oligonucleotides are commonly described as being antisense oligonucleotides. Various reviews describing the results of these studies have been published including Progress In Antisense Oligonucleotide Therapeutics, Crooke, S. T. and Bennett, C. F., *Annu. Rev. Pharmacol. Toxicol.*, 1996, 36, 107–129. These oligonucleotides have proven to be very powerful research tools and diagnostic agents. Further, certain oligonucleotides that have been shown to be efficacious are currently in human clinical trials. Antisense therapy involves the use of oligonucleotides having complementary sequences to target RNA or DNA. The antisense oligonucleotide binds to the target RNA or DNA. Upon binding to the target RNA or DNA, the antisense oligonucleotide can selectively inhibit the genetic expression of these nucleic acids or can induce some other events such as destruction of a targeted RNA or DNA or activation of gene expression.

Destruction of targeted RNA can be effected by RNase H activation. RNase H is an endonuclease that cleaves the RNA strand of DNA:RNA duplexes. This enzyme, thought to play a role in DNA replication, has been shown to be capable of cleaving the RNA component of the DNA:RNA duplexes in cell free systems as well as in Xenopus oocytes.

RNase H is very sensitive to structural alterations in antisense oligonucleotides. To activate RNase H, a DNA:RNA structure must be formed. Therefore for an antisense oligonucleotide to activate RNase H, at least a part of the oligonucleotide must be DNA like. To be DNA like requires that the sugars of the nucleotides of the oligonucleotide have a 2'-deoxy structure and the phosphate linkages of the oligonucleotide have negative charges. Chemical modifications of the DNA portion of oligonucleotide at either of these two positions resulted in oligonucleotides that are no longer substrates for RNase H.

However, 2'-deoxy nucleotides have weaker binding affinity to their counterpart ribonucleotides than like ribonucleotides would, i.e., RNA:RNA binding is stronger than DNA:RNA binding, and the presence of the negative charges has been though to contribute to reduced cellular uptake of the antisense oligonucleotide. Therefore, to circumvent the limitations of DNA like oligonucleotides, chimeric oligonucleotides have been synthesized wherein a DNA like central portion having 2'-deoxy nucleotides and negative charged phosphate linkages is included as the center of a large oligonucleotide that has other types of nucleotides on either side of the DNA like center portion. The center portion must be of a certain size in order to activate RNase H upon binding of the oligonucleotide to a target RNA.

Accordingly, there remains a continuing long-felt need for modified antisense compounds that incorporate chemical modifications for improving characteristics such as compound stability and cellular uptake but are also available for regulation of target RNA through each of the known mechanism of action of antisense compounds including RNase H. Such regulation of target RNA would be useful for therapeutic purposes both in vivo and ex vivo and, as well as, for diagnostic reagents and as research reagents including reagents for the study of both cellular and in vitro events.

SUMMARY OF THE INVENTION

The present invention is directed to oligonucleotides with bioreversible protecting groups that have enhanced chemical and biophysical properties. The bioreversible protecting groups further lend nuclease resistance to the oligonucleotides. The bioreversible protecting groups are removed in a cell, in the cell cytosol, or in vitro in cytosol extract, by endogenous enzymes. In certain preferred oligonucleotides of the invention the bioreversible protecting groups are designed for cleavage by carboxyesterases to yield unprotected oligonucleotides.

The present invention is directed to oligonucleotides having at least one internucleotide linkage of Structure I:

Structure I

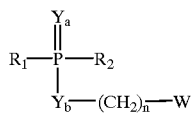

In these oligonucleotides, $Y_a$ and $Y_b$, independently, can be selected as O or S, $R_1$ and $R_2$, independently, are selected as a nucleoside or an oligonucleotide, n is 1 to 6, W is selected as S—S—Z, S—C(=$Y_7$)—Z, or S—C(=$Y_7$)—Z—N($R_5$)($R_6$)($R_7$), Z is hydrocarbyl or substituted hydrocarbyl, $Y_7$ is O or S, and $R_5$, $R_6$, and $R_7$ are, independently, hydrocarbyl.

In preferred oligonucleotides of Structure I, W is selected to be S—C(=Y$_7$)—Z, or S—C (=Y$_7$)—Z—N(R$_5$) (R$_6$) (R$_7$). In other preferred oligonucleotides of Structure I, n is selected to 2 or 4, with 2 being particularly preferred.

In certain preferred oligonucleotides of Structure I, Z is C$_3$–C$_{20}$ alkyl. In a more preferred group, Z is C$_1$–C$_4$ alkyl. Particularly preferred are compounds wherein Z is t-butyl and methyl. R$_5$, R$_6$, and R$_7$ preferably are C$_1$–C$_{20}$ alkyl, more preferably C$_1$–C$_4$ alkyl, even more preferably methyl.

The present invention is also directed to amidite compounds of Structure II:

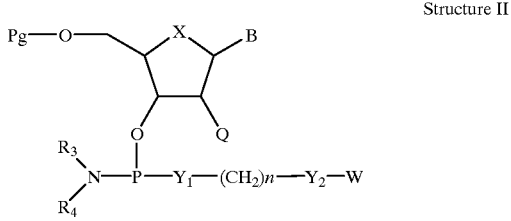

Structure II that are useful as precursors for the preparation of the above oligonucleotide compounds. In these amidite compounds Pg is a nucleoside blocking group, B is a heterocyclic base, Y$_1$ is S and Y$_2$ is O or S or Y$_1$ is O and Y$_2$ is S, R$_3$ and R$_4$, independently, are hydrocarbyl or together R$_3$ and R$_4$ are part of a nitrogen heterocyclic ring, Q is H, OH, F, O-alkyl or O-substituted alkyl, n is 1 to 6, W is S—S—Z, S—C (=Y$_7$)—Z, or S—C(=Y$_7$)—Z—N(R$_5$) (R$_6$) (R$_7$), Z is hydrocarbyl or substituted hydrocarbyl, X is O, S, or CH$_2$, Y$_7$ is O or S, and R$_5$, R$_6$, and R$_7$ are, independently, hydrocarbyl.

In preferred amidite compounds of Structure II, W is selected to be S—C (=Y$_7$)—Z or S—C (=Y$_7$)—Z—N (R$_5$) (R$_6$) (R$_7$). In other preferred oligonucleotides of Structure II, n is selected to 2 or 4 with 2 being particularly preferred.

In further preferred amidite compounds of Structure II, Z is C$_1$–C$_{20}$ alkyl. In a more preferred group, Z is C$_1$–C$_{20}$ alkyl. Particularly preferred are compounds wherein Z is t-butyl and methyl. R$_5$, R$_6$, and R$_7$ preferably are C$_1$–C$_{20}$ alkyl, more preferably C$_1$–C$_4$ alkyl, even more preferably methyl.

In additional preferred amidite compounds of Structure II, B is a purine or pyrimidine such as adenine, guanine, cytosine, uracil or thymine, and Pg is selected trityl, monomethoxytrityl, dimethoxytrityl or trimethoxytrityl. When B includes an exocyclic nitrogen atom (such as, for example, with adenine, guanine, or cytosine), it preferably also bears a protecting group that is covalently bound thereto and removable under basic conditions. Representative protecting groups include pent-4-enoyl, 4-methylsulphinyl-benzyloxycarbonyl, 2-nitrophenylsulfenyl, and triphenyl-methanesulfenyl groups. Particularly preferred are compounds wherein Pg is dimethoxytrityl.

In further preferred amidite compounds of Structure II, each of R$_3$ and R$_4$ is independently selected to be C$_1$–C$_{10}$ alkyl. In particularly preferred amidite compounds of Structure II, each of R$_3$ and R$_4$ are selected to be isopropyl.

In additional preferred groups of amidite compounds of Structure II, Y$_1$ is selected to be O and Y$_2$ is S. In other preferred amidite compounds of Structure II, Y$_1$ is selected to be S and Y$_2$ is O. And in further preferred amidite compounds of Structure II, both Y$_1$ are selected to S.

In preferred deoxy amidite compound of Structure II, Q is H. In further preferred amidite compounds of Structure II, Q is selected as C$_1$–C$_{20}$ O-alkyl and in additional preferred amidite compounds of Structure II, Q is selected to be F.

Further preferred amidite compounds of the invention are compounds of structure III:

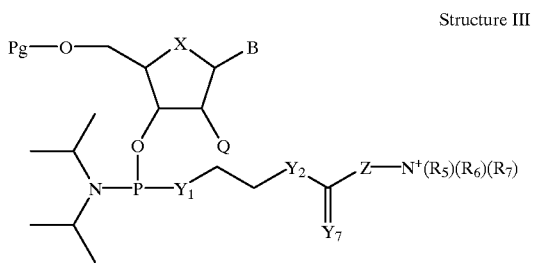

Structure III wherein Pg is a nucleoside blocking group, B is a heterocyclic base, Y$_1$ is S and Y$_2$ is O or S or Y$_1$ is O and Y$_2$ is S, Q is H, OH, F, O-alkyl or O-substituted alkyl, Z is hydrocarbyl or substituted hydrocarbyl, X is O, S, or CH$_2$, Y$_7$ is O or S, and R$_5$, R$_6$, and R$_7$ are, independently, hydrocarbyl.

The present invention also provides support-bound synthons having the structure:

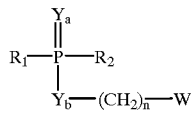

wherein Y$_a$ and Y$_b$, independently, are O or S, R$_1$ is a nucleoside or an oligonucleotide, R$_2$ is L$_p$-(P) where L$_p$ is a photolabile linker and (P) is a solid support, n is 1 to 6, W is S—S—Z, S—C (=Y$_7$)—Z, or S—C(=Y$_7$)—Z—N(R$_5$) (R$_6$) (R$_7$), Z is hydrocarbyl or substituted hydrocarbyl, Y$_7$ is O or S, and R$_5$, R$_6$, and R$_7$ are, independently, hydrocarbyl. In preferred embodiments, L$_p$ is

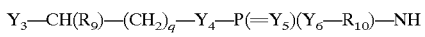

where Y$_3$, Y$_4$, Y$_5$, and Y$_6$ are, independently, O or S, R$_9$ is C$_6$–C$_{20}$ aryl, q is 1–7, and R$_{10}$ is H or a protecting group that is removable under non-basic or non-nucleophilic conditions.

In yet another aspect, the present invention provides functionalized solid supports useful in preparing the compounds of the invention. In preferred embodiments, the solid supports have compound having formula:

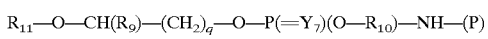

where R$_9$ is C$_6$–C$_{20}$ aryl, q is 1–7, R$_{10}$ is H or a protecting group that is removable under non-basic or non-nucleophilic conditions, R$_{11}$ is an acid-labile protecting group; and (P) is a solid support.

DETAILED DESCRIPTION

Figure 1:
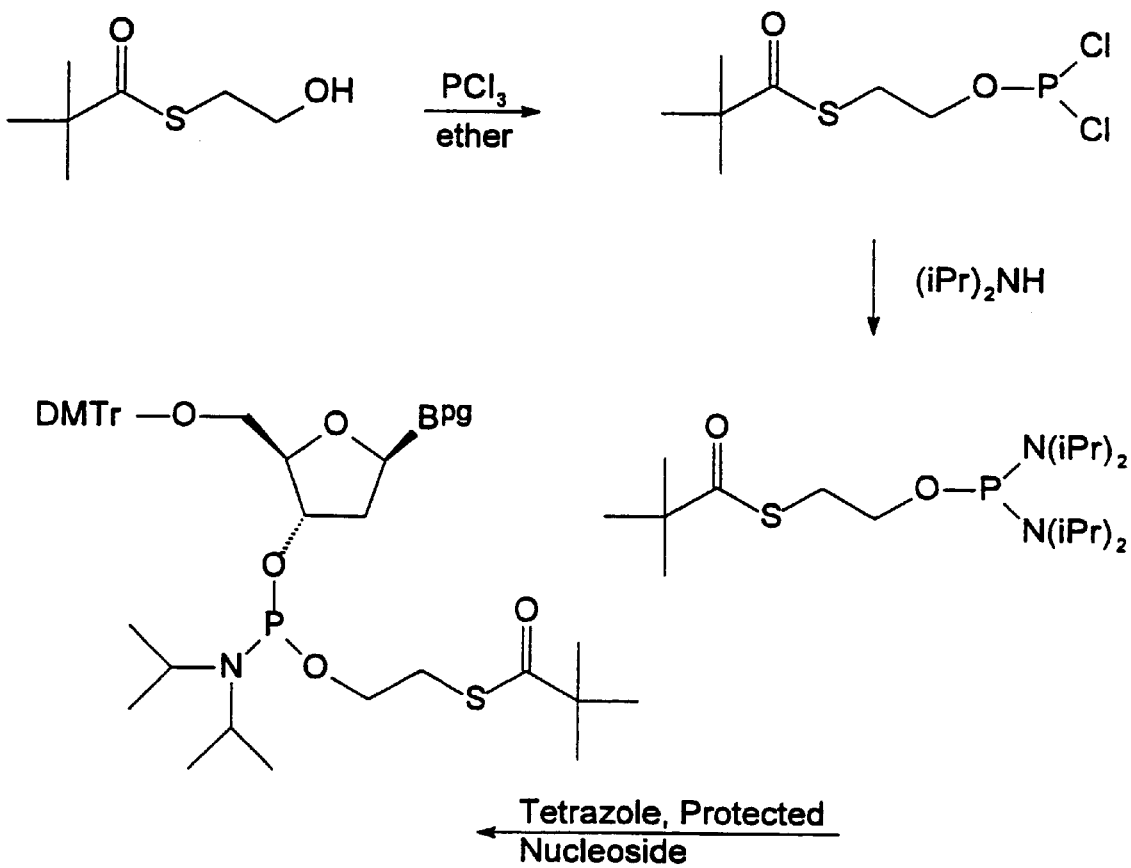
FIG. 1 is a chemical schematic shown preparation of certain illustrative amidite compounds of the invention.

The present invention relates to novel oligonucleotides with bioreversible protecting groups. The bioreversible protecting groups contribute to certain enhanced chemical and biophysical properties of the oligonucleotides including resistance to exo- and endonuclease degradation.

Oligonucleotides (oligos) represent a new class of compounds that specifically inhibit gene expression by Watson-Crick base pair formation with their targets which usually are known mRNA sequences. After binding to the mRNA, downregulation of gene product expression occurs. Crooke, S. T., *Nucleic Acid Therapeutics In Pharmaceutical Manufacturing International,* Sterling, London, 89 (1992). Use of the first synthesized oligonucleotides, i.e., phosphodiester linked oligonucleotides, was limited by the lack nuclease resistance of these compounds. Nuclease resistance has mainly been resolved by the use of modified oligos. Milligan, J. F., et al., *J. Med. Chem.,* 1991, 36, 1923; Varma, R. S., *Synlett,* 1991, 621; Uhlmann, E., et al., *Chem. Rev.,* 1990, 90, 534.

It has been reported that phosphodiester and phosphorothioate oligos, both which have a polyanionic character, enter the cell by an active process (adsorptive endocytosis and/or fluid phase endocytosis) and this uptake varies with different cell types. It has been reported that the neutral methylphosphonodiester oligos enter cells by a different mechanism that is also energy dependent. Spiller, D. G., et al., *Anti-Cancer Drug Design,* 1991, 7, 115. Certain increases in penetration of the oligonucleotides into cell has been achieved by derivatizing oligos with poly L-lysine, cholesterol or other like moieties or by encapsulation into liposomes.

One aspect of this invention is directed to a further approach to assist cellular uptake of oligonucleotides. In this approach a prodrug strategy is utilized wherein a prooligonucleotide is formed that temporarily masks the negative charges of phosphodiester, phosphorothioate and phosphorodithioate oligonucleotides by the introduction of a bioreversible group on at least some of phosphate groups of these oligomers. The resulting neutral prooligos have been found to be enzymatically stable against nucleases. While we do not wish to be bound by theory, we believe this will help oligonucleotides to escape from the endosomes should they become embedded therein and will present a completely different bioavailability pattern in relation with their route of administration. A prerequisite of this approach is that bioreversible groups must be selected that have stability in culture medium and that have selective intracellularly hydrolysis after uptake, due to the existence of a greater enzymatic activity in cytosol than in biological fluids.

The present invention is directed to oligonucleotides with bioreversible protecting groups that have enhanced chemical and biophysical properties for cellular membrane penetration as well as resistance to exo- and endonuclease degradation in vivo. In certain preferred embodiments of the invention, the bioreversible protecting groups are removed in the cell cytosol by endogenous carboxyesterases to yield biologically active oligonucleotide compounds that are capable of hybridizing to and/or having an affinity for specific nucleic acid or peptide sequences thus interacting with endogenous and/or pathogenic biomolecules.

Unless defined otherwise, all technical and scientific terms used herein have the same meaning as is commonly understood by one of skill in the art to which this invention belongs. All publications and patents referred to herein are incorporated by reference.

Oligonucleotide as used herein indicates a DNA or RNA polynucleotide in the ribo- (RNA) or deoxyribo- (DNA), or mixed ribo-deoxyribo, series. Oligonucleotides described herein are formed by a linkage of multiple nucleotides. Preferred oligonucleotides of the invention include at least one bioreversible protecting group to protect internucleotide linkage(s). Preferred oligonucleotides in accordance with this invention preferably comprise from about 5 to about 50 1nucleoside subunits. It is more preferred that the oligonucleotides of the present invention comprise from about 15 to about 25 nucleoside subunits. As will be appreciated, a "nucleoside subunit" is a nucleobase and sugar combination suitably bound to adjacent subunits through phosphorus linkages in the oligonucleotides. In this context, the term "nucleoside subunit" is used interchangeably with the term "nucleoside unit" or "nucleoside." Nucleosides are formed from a sugar moiety and a heterocyclic base moiety. As used in this specification, the term nucleobase will be used interchangeably with heterocyclic base in describing nucleoside components. Nucleotides are used in their normal sense to mean a nucleoside having a phosphate moiety included thereon.

For use in preparing the nucleoside structural subunits of the compounds of the invention, suitable nucleobases for incorporation in these nucleoside subunits include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering,* pages 858–859, Kroschwitz, J. I., ed. John Wiley & Sons, 1990, and those disclosed by Englisch et al., *Angewandte Chemie, International Edition,* 1991, 30, 613. Certain of these nucleobases are particularly useful for increasing the binding affinity of the oligomeric compounds of the invention. These include 5-substituted pyrimidines, 6-azapyrimidines and N-2, N-6 and O -6 substituted purines, including 2-aminopropyladenine, 5-propynyluracil and 5-propynylcytosine. Other modified pyrimidine and purine bases are also expected to increase the binding affinity of oligomeric compounds to a complementary strand of nucleic acid.

The nucleobases of the nucleosides units of the invention can be protected with protecting groups such as, for example, as normally used in standard oligonucleotide synthesis. Typical nucleobase blocking groups have been extensively reviewed in Beaucage, S. L. and Iyer, R. P., *Tetrahedron,* 1992, 48, 2223–2311 and Beaucage, S. L. and Iyer, R. P., *Tetrahedron,* 1993, 49, 6123–6194, Hydrocarbyl groups of the invention include aliphatic, alicyclic and aryl groups. These can be further substituted with various substituent groups.

Aliphatic and alicyclic groups suitable for use in the invention include but are not limited to saturated and unsaturated, straight and branch chain and alicyclic, substituted and unsubstituted alkyl, alkenyl and alkynyl groups including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon straight-chain alkyl groups; 2-methylpropyl, 2-methyl-4-ethylbutyl, 2,4 -diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched- chain groups; vinyl, allyl, crotyl, propargyl, 2-pentenyl and other unsaturated groups; and cyclohexane, cyclopentane, adamantane as well as other alicyclic groups. Preferred compounds are the $C_1$–$C_{20}$ alkyls, $C_1$–$C_{20}$ alkenes and $C_1$–$C_{20}$ alkynes. Most preferred are the $C_1$–$C_4$ alkyls. Particularly preferred are methyl and t-butyl.

Aryl groups suitable for use in the invention include, but are not limited to, phenyl, tolyl, benzyl, naphthyl, anthracyl, phenanthryl and xylyl.

Substituent groups for the above aliphatic, alicyclic and aryl groups include but are not limited to halogen (Cl, Br, F), hydroxyl (OH), thiol (SH), keto (C=O), carboxyl (COOH), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), and nitro (NO). Preferred hydrocarbyl substituent groups includes ether substituents as for instances methoxy substitutions.

For cellular use, for an oligonucleotide to be particularly useful, the oligonucleotide must be reasonably stable to nucleases in order to survive in cells for a time period sufficient for it to interact with target nucleic acids of the cells. Therefore, in certain embodiments of the invention, specific nucleoside subunits or internucleoside linkages are functionalized or selected to increase the nuclease resistance of the oligonucleotide. However, for non-cellular uses, such as use of oligomeric compounds of the invention as research reagents and as diagnostic agents, such nuclease stability may not be necessary.

A further useful property of an oligonucleotide is binding affinity. In determining the extent of binding affinity of a first nucleic acid to a complementary nucleic acid, the relative ability of the first nucleic acid to bind to the complementary nucleic acid may be compared by determining the melting temperature of a particular hybridization complex. The melting temperature ($T_m$), a characteristic physical property of double stranded nucleotides, denotes the temperature (in degrees centigrade) at which 508 helical (hybridized) versus coil (unhybridized) forms are present. $T_m$. is measured by using the UV spectrum to determine the formation and breakdown (melting) of the hybridization complex. Base stacking which occurs during hybridization is accompanied by a reduction in UV absorption (hypochromicity). Consequently, a reduction in UV absorption indicates a higher $T_m$. The higher the $T_m$, the greater the strength of the bonds between the strands.

One way to improve nuclease resistance of an oligonucleotide is to modify the phosphate linkages that connect adjacent nucleotides in the oligonucleotide. Such modifications include phosphorothioate, phosphorodithioate, methyl phosphonate, alkyl phosphate, phosphoramidites, phosphotriester and other like modifications.

A further way to increase nuclease resistance is by the inclusion of substitutions at the 2' position of at least some of nucleotides of the oligonucleotide. Such 2' substitutions also serve, in some instances, to improve the binding affinity of the oligonucleotide for a target RNA. Particularly useful 2'-substituents are 2'-O-alkyl substituents. The smaller members of this group contribute to increases in binding affinity while the larger members contribute to increases in nuclease stability. A further particularly useful 2'-substituent group for increasing the binding affinity is the 2'-fluoro group as was noted in a published study: (*Synthesis and Biophysical Studies of 2'-dRIBO-F Modified Oligonucleotides*, Conference On Nucleic Acid Therapeutics, Clearwater, Fla., Jan. 13, 1991).

This invention provides oligonucleotides having bioreversible protecting groups that contribute to enhanced chemical and biophysical properties for cellular membrane penetration as well as resistance to exo- and endonuclease degradation.

The invention further provided amidite reagents for the synthesis of the bioreversible protected oligonucleotides. Because synthetic processes according to the present invention must avoid basic or nucleophilic conditions due to the susceptibility of phosphotriester groups to hydrolysis, amidite reagents which include nucleobases with protecting groups that are removable under non-basic or non-nucleophilic conditions should be used. Moreover, these protecting groups should be stable during all of the synthetic processes. Numerous such protecting groups are well-known to those skilled in the art (see, e.g., Greene and Wuts, Protective Groups in Organic Synthesis, 2d edition, John Wiley & Sons, New York, 1991. Representative amine protecting groups include the pent-4-enoyl, 4-methylsulphinyl-benzyloxycarbonyl, 2-nitrophenylsulfenyl, and triphenyl-methanesulfenyl groups.

It has been found in accordance with the invention that the use of base to effect release of an oligonucleotide from a solid support can be avoided through use of a photolabile linker. In preferred embodiments, the support-bound oligonucleotide has Structure I wherein $R_2$ is $L_p$-(P) where $L_p$ is a photolabile linker and (P) is the solid support. In preferred embodiments, $L_p$ has structure

Figure 4:
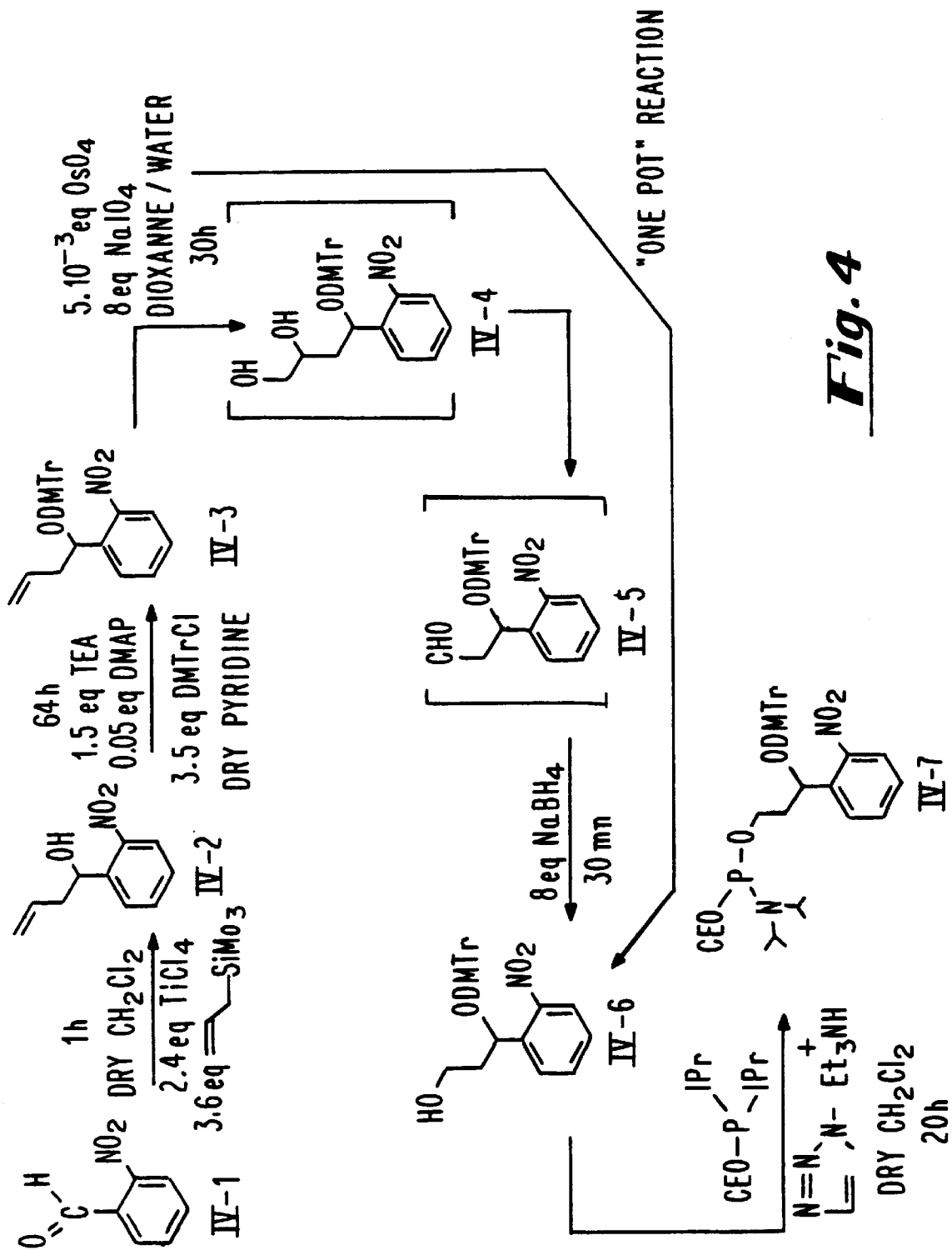
FIG. 4 shows synthetic routes for compound IV-7.
Figure 5:
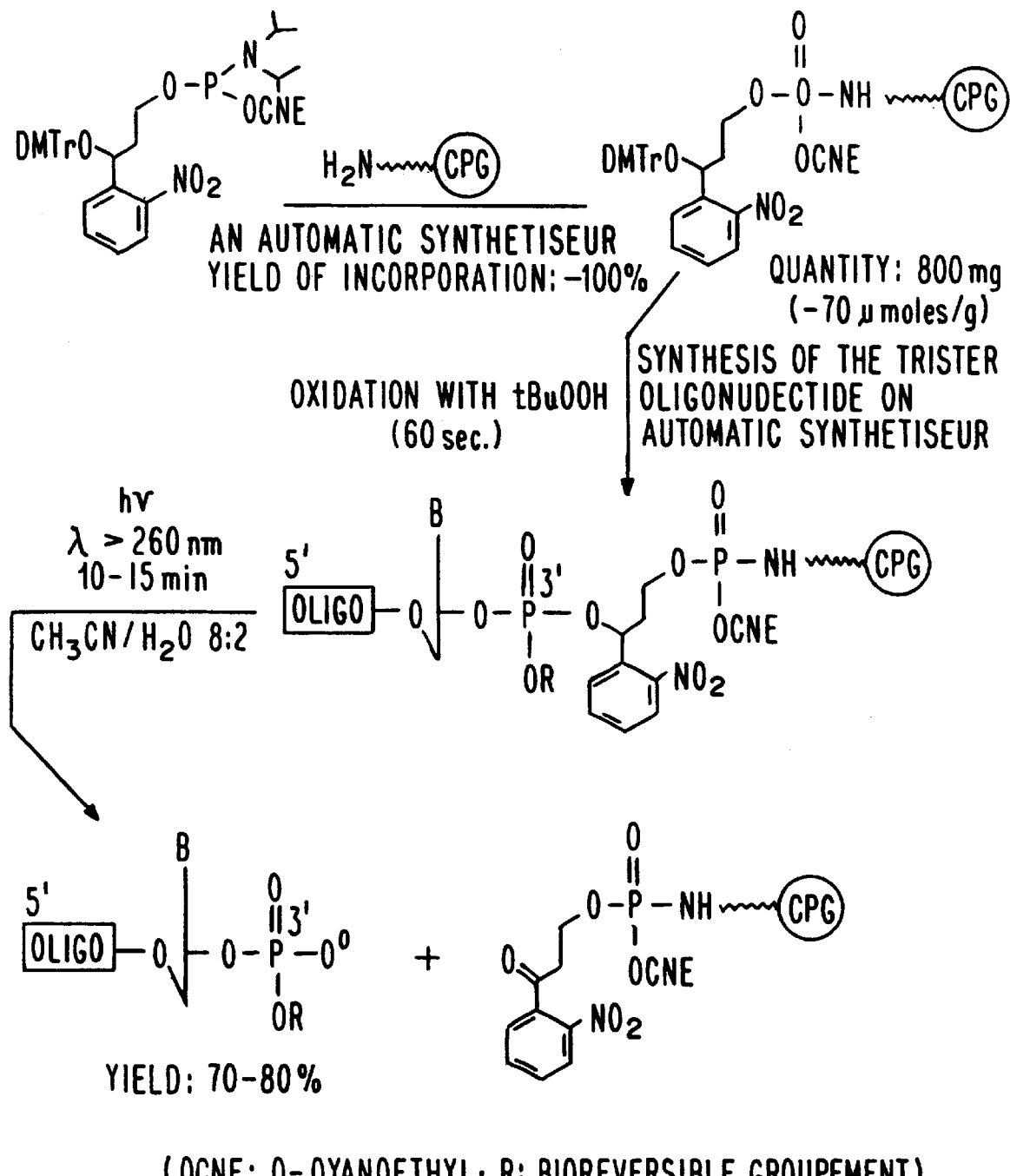
FIG. 5 shows synthetic routes for use of compound IV-7.

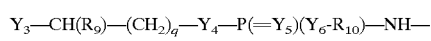

and is introduced into the compounds of the invention through reaction of a nucleoside or oligonucleotide with a reagent having structure:

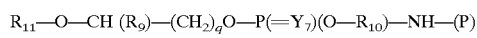

where $Y_3$, $Y_4$, $Y_5$, and $Y_6$ are, independently, O or S, $R_9$ is a photolabile group such as, for example, a nitro-substituted $C_6$–$C_{20}$ aryl group, q is 1–7, $R_{10}$ is H or a protecting group that is removable under non-basic or non-nucleophilic conditions such as cyanoethyl, $C_1$–$C_{20}$ alkyl, or $C_6$–$C_{20}$ aryl, and $R_{11}$ is an acid-labile protecting group such as methoxytrityl, dimethoxytrityl or pixyl. Solid supports according to the invention include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene. Representative synthetic procedures for the linking moiety and use thereof in oligonucleotide synthesis are shown in FIGS. 4 and 5.

The oligonucleotides of the invention having bioreversible protecting groups are also referred to in this specification as pro-oligonucleotides. In preferred embodiments of this invention, the pro-oligonucleotides of the present invention are capable of improved cellular lipid bilayers penetrating potential as well as resistance to exo- and endonuclease degradation in vivo. In cells, the bioreversible protecting groups are removed in the cell cytosol by endogenous carboxyesterases to yield biologically active oligonucleotide compounds that are capable of hybridizing to and/or having an affinity for specific nucleic acid.

The present invention mitigates the major problems with the therapeutic use of oligonucleotides of natural composition, i.e., phosphodiester oligonucleotides, namely 1) their very short biological half-lives due to degradation by nucleases which tend to be ubiquitous, and 2) their inherent negative charge and hydrophilic nature which makes it very difficult biophysically for oligos to pass through lipid cellular membranes.

As practiced herein, the pro-oligonucleotides may be antisense oligonucleotides of synthetic DNA or RNA or mixed molecules of complementary sequences to a target sequence belonging to a gene or to an RNA messenger whose expression they are specifically designed to block or down-regulate. The antisense oligonucleotides may be directed against a target messenger RNA sequence or, alternatively against a target DNA sequence, and hybridize to the nucleic acid to which they are complementary. Accordingly, these molecules effectively block or down-regulate gene expression.

The pro-oligonucleotides may also be directed against certain bicatenary DNA regions (homopurine/homopyrimidine sequences or sequences rich in purines/pyrimidines) and thus form triple helices. The formation of a triple helix, at a particular sequence, can block the interaction of protein factors which regulate or otherwise control gene expression and/or may facilitate irreversible damage to be introduced to a specific nucleic acid site if the resulting oligonucleotide is made to possess a reactive functional group.

In the context of this invention, a target nucleic acid shall mean any nucleic acid that can hybridize with a complementary nucleic acid like compound. Further in the context of this invention, "hybridization" shall mean hydrogen bonding, which may be Watson-Crick, Hoogsteen or reversed Hoogsteen hydrogen bonding, between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

Compounds of the invention can be utilized as diagnostics, therapeutics and as research reagents and kits. They can be utilized in pharmaceutical compositions by adding an effective amount of a compound of the invention to a suitable pharmaceutically acceptable diluent or carrier. They further can be used for treating organisms having a disease characterized by the undesired production of a protein. The organism can be contacted with a compound of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered a compound in accordance with the invention, commonly in a pharmaceutically acceptable carrier, in doses ranging from 0.01 $\mu$g to 100 g per kg of body weight depending on the age of the patient and the severity of the disease state being treated. Further, the treatment regimen may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the compound say either be increased in the event the patient does not respond significantly to current dosage levels, or the dose may be decreased if an alleviation of the symptoms of the disease state is observed, or if the disease state has been ablated.

In some cases it may be more effective to treat a patient with a compound of the invention in conjunction with other traditional therapeutic modalities. For example, a patient being treated for a viral disease may be administered a compound of the invention in conjunction with a known antiviral agent, or a patient with atherosclerosis may be treated with a compound of the invention following angioplasty to prevent reocclusion of the treated arteries.

Following successful treatment, it may be desirable to have the patient undergo maintenance therapy to prevent the recurrence of the disease state, wherein the compound of the invention is administered in maintenance doses, ranging from 0.01 $\mu$g to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}s$ found to be effective in in vitro and in vivo animal models. In general, dosage is from 0.01 µg to 100 g per kg of body weight, and may be given once or more daily, weekly, monthly or yearly, or even once every 2 to 20 years.

Oligonucleotides of the invention may be synthesized conveniently and routinely, through the well-known technique of solid state synthesis, to be complementary to a preselected nucleotide sequence of the RNA or DNA. Nucleic acid synthesizers are commercially available and their use is generally understood by persons of ordinary skill in the art as being effective in generating nearly any oligonucleotide of reasonable length which may be desired.

Oligonucleotide are synthesized by a standard solid phase, automated nucleic acid synthesizer such as the Applied Biosystems Incorporated 380B or MilliGen/Biosearch 7500 or 8800. Triester, phosphoramidite, or hydrogen phosphonate coupling chemistries described in, for example, M. Caruthers, Oligonucleotides: Antisense *Inhibitors of Gene Expression.,* pp. 7–24, J. S. Cohen, ed. (CRC Press, Inc. Boca Raton, Fla., 1989) or Oligonucleotide synthesis, a practical approach, Ed. M. J. Gait, IRL Press, 1984; "Oligonucleotides and Analogues, A Practical Approach", Ed. F. Eckstein, IRL Press, 1991, are employed by these synthesizers to provide the desired oligonucleotides. The Beaucage reagent, as described in, for example, *Journal of American Chemical Society,* 1990, 112, 1253–1255, or elemental sulfur, as described in Beaucage et al., *Tetrahedron Letters,* 1981, 22, 1859–1862, is used with phosphoramidite or hydrogen phosphonate chemistries to provide substituted phosphorothioate oligonucleotides.

For use with phosphoramidite chemistry, various amidite reagents are commercially available, including 2'-deoxy amidites, 2'-O-methyl amidites and 2'-O-hydroxyl amidites. Any other means for such synthesis may also be employed. The actual synthesis of the oligonucleotides is well within the talents of those skilled in the art. It is also well known to use similar techniques to prepare other oligonucleotides such as the phosphorothioates, methyl phosphonates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

In practicing phosphoramidite chemistry to prepare oligonucleotides, multiple reaction conditions, supports and reagents are known from the published work of M. Caruthers and S. Beaucage and others, as described above, as well from the following United States patents including U.S. Pat. Nos. 4,458,066, 4,500,707, 5,132,418, 4,415,732, 4,668,777, 4,973,679, 5,278,302, 5,153,319, 5,218,103, 5,268,464, 5,000,307, 5,319,079, 4,659,774, 4,672,110, 4,517,338, 4,725,677 and Re. 34,069, each of which is herein incorporated by reference. Additionally, the practice of phosphoramidite chemistry has been systematically reviewed by Beaucage and Iyer in Beaucage, S. L. and Iyer, R. P., *Tetrahedron,* 1992, 48, 2223–2311 and Beaucage, S. L. and Iyer, R. P., *Tetrahedron,* 1993, 49, 6123–6194, or references referred to therein, all of which is herein incorporated by reference.

In practicing phosphoramidite chemistry particularly useful sugar blocking groups, i.e., Pg groups, are trityl, momomethoxytrityl, dimethoxytrityl and trimethoxytrityl, especially dimethoxytrityl (DMTr). In practicing phosphoramidite chemistry particularly useful phosphite activating groups, i.e., $NR_3R_4$ groups, are dialkyl substituted nitrogen groups and nitrogen heterocycles as described in the above reference Caruthers patents. Particularly useful is the di-isopropylamino activating group.

Various nucleotide units can be can be activated as amidites of the invention and incorporated in to the oligonucleotides of the inventions. These include deoxy nucleotides, i.e., wherein Q in the above structures is H, ribonucleotides, i.e., wherein Q is OH in the above structures, 2'-alkoxy nucleotides, i.e., wherein Q is O-alkyl in the above structures, or substituted 2'-O-alkyl nucleotides, i.e., wherein Q is substituted -O-alkyl in the above structures. 2'-O-alkyl nucleotides are described in U.S. Pat. No. 5,466,786, herein incorporated by reference. A particularly useful substituted 2'-O-alkyl group, the methoxyethoxy group, is described by Martin, P., *Helv. Chim. Acta,* 1995, 78, 486–504, also herein incorporated by reference.

For intercellular delivery of 5'-mononucleotides we have used the methyl S-acylthioethyl, also referred to herein as Me-SATE, bioreversible protecting group. When used to protect a mononucleoside phosphate, we have demonstrated that through a carboxyesterase mediated decomposition process, selective recovery of the nucleoside monophosphate was possible. Lefebvre, I., et al., *J. Med. Chem.* (1995).

In the examples below we describe the use of two different dithymidine models (i.e., phosphate and phosphorothionate triesters, a phosphotriester dimer (compound 1, FIG. 3) and a phosphothionotriester dimer (compound 2, FIG. 3). The dithymidine phosphate and phosphorothionate were prepared as triesters bearing a tert-butyl S-acylthioethyl (tBu-SATE) bioreversible protecting group, i.e., compounds 1 and 2). Their stability in culture medium (CM) and in total CEM cell extract (TCE) was evaluated.

These dimers are shown to have a high stability in CM and are selectively hydrolyzed in TCE by carboxyesterase activities to the corresponding parent dimer. The stabilities, were evaluated by HPLC monitoring, in culture medium and in total CEMSS cell extract upon incubation conditions. The tert-butyl-S-acylthioethyl protecting group (tBu-SATE) was selected as the bioreversible group on the basis of its pharmacokinetic parameters. Hydrolysis via carboxyesterase attack of compound 1 results in the corresponding phosphodiester dimer whereas compound 2 results in the phosphorothioate analog.

The prooligonucleotides of the invention can be hydrolyzed through two mechanisms involving either a P-X (nucleophilic attack on phosphorous atom) or a C-X (nucleophilic attack on carbonyl function mediated by carboxyesterases) bond breakage process depending on the affinity of the substrate for carboxyesterases, the nucleophilicity of the reagents, and the nature of the leaving group.

Nonionic oligonucleotide methylphosphonates, or similar alkyl or aryl phosphonates, are well known to those skilled in the art for use as chemically synthesized analogs of nucleic acids that can easily pass through the membranes of living cells and are resistant to degradation or hydrolysis by nucleases while having a relatively long biological half-life in vivo. See, U.S. Pat. No. 4,511,713, which is herein incorporated by reference. Although methylphosphonate oligos tend to present low binding capacities with targeted RNA, they are contemplated to be used in combination with phosphodiester or phosphorothionate internucleosidic linkage prooligonucleotides of the present invention.

The synthesis of dithymidine compounds 1–2 was carried out following a simple reaction scheme. The dithymidine phosphoramidite was condensed with tert-butyl-S-acyl-thioethanol in the presence of tetrazole in acetonitrile to yield the resulting phosphite triester, which was finally oxidized by tert-butyl hydroperoxide or by elemental sulfur to give respectively, after deprotection of the 5' and 3'-hydroxyls, the respective dimers.

Oligonucleotides were synthesized on an Applied Biosystems 381A or 380B DNA Synthesizers. The $^1$H and $^{31}$P NMR spectra were recorded with a Bruker AC 250 (250 MHZ) spectrometer. $^1$H and $^{31}$P NMR chemical shifts were measured relative to $CDCl_3$, $CD_3COCD_3$ or $CD_3CN$ taken as internal reference. Fast atom Bombardment Mass Spectra (MS) were recorded on a Jeol Dx 300 Mass Spectrometer in positive or negative ion mode using a thioglycerol (GT) or 3 nitrobenzylalcohol (NBA) matrix. Thin layer chromatography was carried out using Kieselgel $60F_{254}$ plates (E. Merck), with detection by UV light and sulfuric acid spray. Silica gel 60 was used for column chromatography. Stabilities of the triesters were determined by HPLC using on-line cleaning method with a reverse-phase $C_{18}$ column (3 µm, Hypersil, 150×4.6 mm), with a gradient of 100% A to 100% B in 40 min, (A: 0.05M TEAAc; pH=7.0; B: 50:50 $CH_3CN$:0.05M TEAAc; Flow rate: 1 ml/min). For each time-point, a 100 µl aliquot of medium (medium culture= RPMI 1640+10% calf foetal serum or total cell extract) containing a dimer phosphotriester (5 $10^{-5}$M) or an prooligonucleotide ($10^{-5}$M) with 0.5% of DMSO was incubated at 37° C. prior injection.

The following examples and procedures illustrate the present invention and are not intended to limit the same.

EXAMPLE 1
Oligonucleotide synthesis

Unsubstituted and substituted phosphodiester oligonucleotides are synthesized using standard phosphoramidite chemistry with oxidation by iodine.

Phosphorothioate oligonucleotides are synthesized as per the phosphodiester oligoribonucleotides except the standard oxidation bottle is replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step.

After cleavage from the CPG column and deblocking in concentrated ammonium hydroxide at 55° C. (18 hr), the oligonucleotides were purified by precipitating twice with 2.5 volumes of ethanol from a 0.5 M NaCl solution. Analytical gel electrophoresis was accomplished in 20% acrylamide, 8 M urea, 454 mM Tris-borate buffer, pH=7.0. Oligonucleotides and phosphorothioates were judged, based on polyacrylamide gel electrophoresis, to be greater than 80% full-length material.

Alkyl phosphonate oligoribonucleotides are prepared as is described in U.S. Pat. No. 4,469,863, herein incorporated by reference.

EXAMPLE 2
Synthesis of phosphotriester dimer 1

Figure 2:
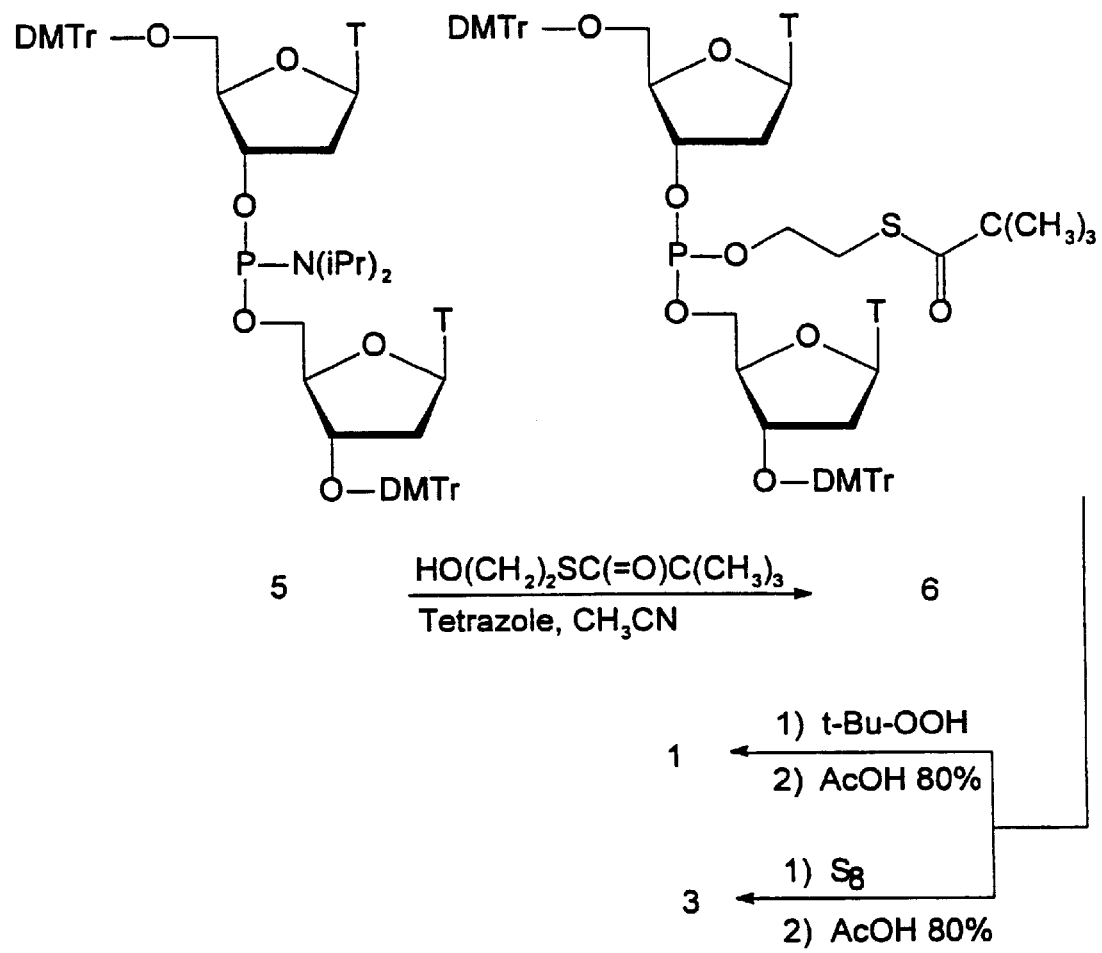
FIG. 2 is a chemical schematic shown preparation of certain illustrative oligonucleotide compounds of the invention.

Bisthymidinediisopropylaminophosphine 5 (FIG. 2) (0.1 mmol, 122 mg) and tert-butyl-S-acyl-thioethanol (0.12 mmol, 19 mg) are stirred together in 3 ml dry $CH_3CN$ with molecular sieves for 2 h before addition of sublimated tetrazole (0.3 mmol, 21 mg). After 4 h at room temperature, tert-butylhydroperoxide (0.24 mmol, 82 µl is added. The mixture is stirred 1.5 h at room temperature, then extracted between saturated aq $Na_2S_2O_3$ and $CH_2Cl_2$. After evaporation, the residue is purified by chromatography on a silica gel column ($CH_2Cl_2$+1% TEA) yielding 6 (FIG. 2) (90.6 mg, 70%). Dimethoxytrityl groups are cleaved by treatment with 80% $AcOH/H_2O$ (1 ml) for 3.5 h. dimer phosphotriester 1 was purified by HPLC and fully characterized. $^1$H NMR ($CD_3OD$) δ (ppm): 6.3 (2H,m, 2×$H_1$'); 4.15 (2Hq,$CH_2OH$); 3.15 (2H,t,$CH_2S$); 1.85 (6H,m, 2×$CH_3dT$); 1.2 (9H,m,C($CH_3$)$_3$); residue 5'OH-dT-3'OP: 4.45 (1H,m,H3'); 4.35 (2H,m,$H_5$',$H_5$"), 4.2 (1H,m,$H_4$'); 2.25 (2H,t,$H_2$',$H_2$"); residue 3'OH-dT-5'OP: 5.15 (1H,m,H3'); 4.05 (1H,m,$H_4$'); 3.75 (2H,m,H5',H5"); 2.3–2.6 (2H,m,$H_2$', $H_2$") $^{31}$P-NMR: ($CD_3OD$) −2.28 and −2.35 ppm, MS FAB pos m/z $[M+H]^+$: 691.

EXAMPLE 3
Synthesis of phosphothionotriester dimer 2

Dimer phosphothionotriester 2 is synthesized by the same procedure as in Example 1 except that oxidation reaction is performed with elemental sulfur (0.5 mmol, 16 mg) in $CH_3CN$ for 2 h. The work-up includes an extraction between $H_2O$ and $CH_2Cl_2$. The residue is purified by chromatography on a silica gel column (10 to 100% $CH_2Cl_2$ in cyclohexane +1% $NEt_3$). Finally dimer phosphothionotriester 2 (0.07 mmol, 92 mg) is obtained with 70% yield after detritylation. $^1$H NMR ($CD_3OD$): δ (ppm): 6.3 (2H,m,2×$H_1$'); 3.15 (2H, t,$CH_2S$); 1.85 (6H,m,2×$CH_3dT$); 1.20 (9Hm,C($CH_3$)$_3$); 5.10 (1H, m, $H_3'_{OH}$); 4.00–4.40 (7H,m,$H_3'_{OP}$,$H_5$'$H_5$"$_{OH}$,2×4', $CH_2OH$) 3.75 (2H,s,$H_5$'$H_5$"$_{OP}$);2.1–2.6 (4Hm,2$H_2$',2×$H_2$") 4.15 (2H,q,$CH_2OH$). $^{31}$P-NMR: ($CD_3OD$) 67.40 and 67.43 ppm, MS FAB pos m/z $[M+H]^+$: 707;

EXAMPLE 4
Synthesis of chimeric oligonucleotides

5'-0-DMTr-thymidine-3'-yl-S-(p-thiobenzoylethyl) pyrrolidinophosphorothioamidite was synthesized following the Caruthers procedure (94% purity by $^{31}$P NMR, 166.71 and 163.04 ppm). Wiesler, W. T., et al., *Synthesis and Purification of Phosphorodithioate DNA*, Humana Press, Totowa, N.J., 191 (1993). Chimeric methylphosphonodiester/phosphorothioate and methylphosphonodiester/phosphorodithioate oligodeoxynucleotides were synthesized on a DNA synthesizer using methylphosphonamidite, β-cyanoethylphosphor-amidite or thiophosphoramidite synthons. A solution of iodine-water-pyridine-THF (0.1M:1:10:40) as oxidizer agent or a solution of Beaucage reagent (3H 1,2-benzodithiol-3-one 1,1-dioxide) as sulfurization agent. Syntheses were achieved with an oxalyl linker (Alul, R. H., et al., *Nucl. Acids Res.*,1991, 19, 1527) between the LCAA-CPG solid support and the oligomer, to have a final quick removal, in order to avoid concentrated ammonium hydroxide treatment that degrades methylphosphonate backbones. See, also, Barber, I., et al., *Bioorg. Med. Chem. Lett.*, 1995, 5, 1441. The oligonucleotides were purified by HPLC using a C-18 reverse phase column using increasing amount of acetonitrile in triethylammonium acetate (0.05M, pH 7.0) as eluent.

EXAMPLE 5
Post synthetic oligodeoxynucleotide alkylation

SATE alkylation of oligonucleotides (130 μl, 1.5 mM in water) is performed with 60 eq of MeSATE iodide (12.5 μl, 940 mM in acetonitrile) and 2,6-lutidine (60 μul, 100 mM in acetonitrile) in acetonitrile (57 μl). The reaction is monitored by HPLC, after observation of the transitory formation of the mono and dialkylated products, the fully alkylated prooligo is formed in nearly quantitative yield and is obtained pure after purification by HPLC and desalting on SEP PAK C18.

POM alkylation of oligonucleotides (30 μl, 7.2 mM in water) is performed with 48 eq. of POM iodide derivative (15 μl, 690 mM in acetonitrile) and lutidine (15 μl, 690 mM in acetonitrile) in acetonitrile/water (240 μl, 1:1, v/v) at room temperature (3 h). The expected biotin conjugated prooligo is isolated after purification by HPLC and desalting on SEP PAK C18.

EXAMPLE 6
S-pivaloyl thioethyl N,N-diisopropyl phosphoramidite

To a dry flask containing ether (300 mL) phosphorous trichloride (18.54 g, 135 mmol) was added dropwise under argon atmosphere with external cooling. The alcohol, S-pivaloylthioethyl alcohol (tBuCOS—$CH_2$—$CH_2$—OH) 100 mmol was added as an ether solution (100 mL) dropwise over a period of one hour. After the addition, the reaction flask was brought to room temperature and the reaction mixture was stirred for four hours. The ether is evaporated partially from the reaction mixture and to this dicholoro-phophorus derivative of the alcohol in ether (200 mL) was added diisopropylamine 116 mmol at 0° C. under argon. After the addition was complete (one hour) the reaction mixture is stirred overnight. Concentration of the ether solution provided the phosphoramidite of the alcohol derivative $^{31}P$ NMR: 123 ppm.

EXAMPLE 7
5'-O-(dimethoxytrityl)thymidine-3'-O-(S-pivaloyl thioethyl N,N-diisopropyl) phosphoramidite B=T To an oven-dried flask containing 5'-O-DMT-thymidine (3.81 g, 7 mmol) is added 100 mL anhydrous acetonitrile followed by 6 mmol of tetrazole. The solution is stirred and to this is added pivaloylthioethyl N,N-diisopropyl phosphoramidite (11 mmol). After stirring for four hours $^{31}P$ NMR of the reaction showed partial disappearance of 123 ppm peak and appearance of the derived amidite around 150 ppm. TLC indicated complete consumption of the nucleoside and formation of desired amidite. The reaction mixture was concentrated and directly applied to a silica gel column and eluted with 50:50 ethyl acetate:toluene which has traces of triethylamine. The product was pooled from the column fractions.

EXAMPLE 8
N2-Isobutyryl-5-O-(dimethoxytrityl)-2'-deoxyguanosine-3'-O-(S-pivaloyl thioethyl N,N-diisopropyl) phosphoramidite B=dG The procedure under Example 7 is repeated with $N^2$-isobutyryl-5'-O-dimethoxytrityl-2'-deoxyguanosine in place of thymidine derivative to yield the desired amidite.

EXAMPLE 9
N6-Benzoyl-5'-O-dimethoxytrityl-2'-deoxyadenosine-3'-O-(S-pivaloyl-S-ethyl N,N-diisopropyl phosphoramidite) B=dA The procedure in Example 7 is repeated with $N^6$-Benzoyl-5'-O-dimethoxytrityl-2'-deoxyadenosine nucleoside in place of 5'-O-dimethoxytrityl-thymidine to give the desired amidite.

EXAMPLE 10
N4-benzoyl-5'-O-dimethoxytrityl-2'-deoxycytidine-3'-O-(S-pivaloyl-S-ethyl N,N-diisopropyl) phosphoramidite B=dC The procedure in Example 7 is repeated using $N^4$-benzoyl-5'-O-dimethoxytrityl-2'-deoxycytidine in place of 5'-O-dimethoxytrityl-thymidine to yield the desired amidite.

EXAMPLE 11
Carboxyesterase activity

Figure 3:
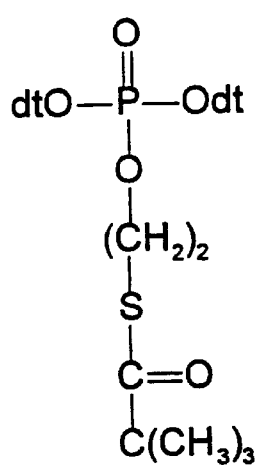
FIG. 3 illustrates certain oligonucleotide compounds of the invention.
Figure 3:
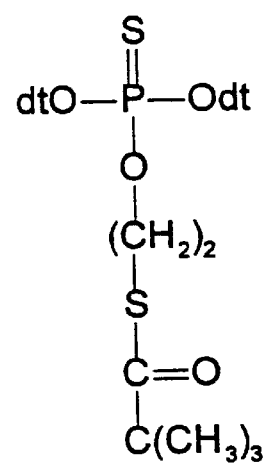
Figure 3:
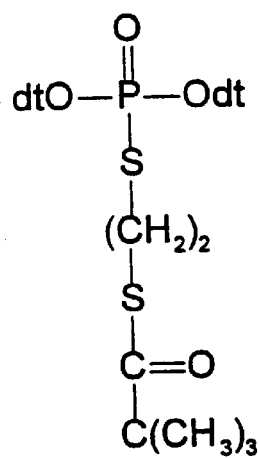
Figure 3:
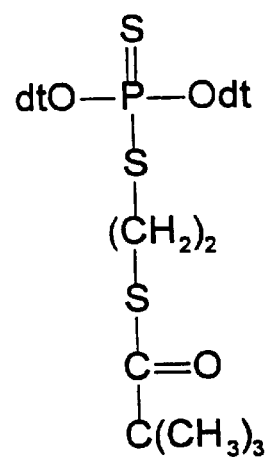

In this example two different dithymidine models (i.e., phosphate and phosphorothionate triesters, a phosphotriester dimer, compound 1, FIG. 3, and a phosphothionotriester dimer, compound 2, FIG. 3) are compared. The dithymidine phosphate and phosphorothionate were prepared as triesters bearing a tert-butyl S-acyl-thioethyl (tBu-SATE) bioreversible protecting group, i.e., compounds 1 and 2). Their stability in culture medium (CM) and in total CEM cell extract (TCE) was evaluated. These dimers were found to have a high stability in CM and are selectively hydrolyzed in TCE by carboxyesterase activities to the corresponding parent dimer. The stabilities, were evaluated by HPLC monitoring, in culture medium (RPMI 1640+10% of heat inactivated fetal calf serum) and in total CEMSS cell extract upon incubation conditions. Hydrolysis via carboxyesterase attack of compound 1 results in the corresponding phosphodiester dimer whereas compound 2 results in the phosphorothioate analog.

The stability of each dimer, in culture medium and in total cell extract (as a model for intracellular medium) was evaluated, using the HPLC cleaning method (Pompon, A., et al., *Biochem Pharmacol.*, 1992, 43, 1769, which is incorporated herein by reference). Their half lives were determined as summarized in Table I with identification of the corresponding hydrolysis products. In each case two values of half-lives are given which correspond to the half-life of each diastereoisomer of the dimer. Such an enantiomeric dependence has been reported for the hydrolysis of $R_p$ and $S_p$ methylphosphonothioate mediated by acetylcholine esterase. Zhao, Q., et al., *Biochemistry*, 1994, 33, 8128.

TABLE I

| DIMER COMPOUND | 1 | 2 |
| --- | --- | --- |
| CULTURE MEDIUM | 32h/34h | 114h/169h |
|  | POO$^-$ | POS$^-$ |
| TOTAL CEM | 15.4 ± 6.0h/ | 7.6 ± 0.3h/ |
| CELL EXTRACT | 15.4 ± 2.2h | 6.9 ± 1.9h |
|  | POO$^-$ | POS$^-$ |

The two triester dimers exhibit a high stability in culture medium (t 1/2 from 32 h to 169 h). The observed selective formation of dithymidine phosphorothioate from compound 2 in total CEM cell extract may thus be explained not by a nucleophilic attack on the phosphorous atom but by a carboxyesterase mediated decomposition process. It has previously been shown that there is residual carboxyesterase activity in the culture medium. The oxo triester (compound 1) is more prone to a nucleophilic attack on the phosphorous atom and give rise to a shorter half-life than the corresponding thiono (compound 2). Compound 2, in fact is more stable in culture medium than tested compounds 3 and 4 of the prior art. The observed stability order in culture medium is 2>4>1>3.

In total CEM cell extract the decomposition process is mediated by carboxyesterases. This point is corroborated by exclusive formation of the phosphorothioate dimer from compound 3. The observed stability data (1>2>3>4) reflects the affinity of the phosphotriesters for the enzymes, where the more lipophilic dimer is a better substrate.

EXAMPLE 12
Chimeric oligonucleotides having bioreversible blocking groups

Two chimeric oligonucleotides were synthesized and were evaluated for stability by HPLC. The first oligonucleotide was a dodecamer phosphorodithioate oligonucleotide having Me-SATE protection groups. The oligonucleotide was synthesized having a central gap of three phosphorodithioate linkages and two neutral methylphosphonate flanks. A post-synthetic strategy was used to synthesize the oligonucleotide to avoid instability of phosphotriester derivatives under basic conditions. The oligonucleotide was selectively alkylated on each phosphorodithioate with Me-SATE iodide, and the resulting neutral chimeric oligonucleotide was purified by HPLC on a reverse phase $C_{18}$ column. The stability of the oligonucleotide was evaluated in culture medium and in total CEM cell extract. In each case, the hydrolysis yielded selectively the parent oligonucleotide (the oligonucleotide with out the Me-SATE blocking groups) with a good stability in culture medium (t ½=32 h). In cell extract, the hydrolysis of the first bioreversible group took place with a half-life of 15 min. and the fully deprotected oligonucleotide was obtained with a half-life of 80 min. No difference in deprotection rate for the second and the third Me-SATE group was observed.

For comparative purposes, the second chimeric oligonucleotide was prepared having a central gap of three phosphorothioate linkages alkylated with the pivaloyloxymethyl (POM) bioreversible protecting group and two methylphosphonate flanks. Again the post-synthetic strategy was used for introducing the phosphate blocking groups. In this case, oligonucleotide was labeled with biotin as reporter group in order to later determine the localization of oligonucleotide in cells, by spectrofluorometry. As for the first oligonucleotide, the stability of the second oligonucleotide was evaluated in culture medium and in total CEM cell extract. Its half-lives found to be 4.5 h in culture medium. As compared to the first oligonucleotide, an oligonucleotide of the invention, in this case selective formation of the parent oligo due to a competitive nucleophilic attack on the phosphorous atom was as not observed. In total cell extracts, the successive removal of the POM groups was monitored by HPLC. It was observed that the first protecting group was removed very rapidly ($t_{1/2}$ <2 min.), while the deprotection of the remaining POM groups proceeded much more slowly, i.e. the half-life for complete apparition of the fully deprotected chimeric oligo was 2.4 h.

The observed differences in the rates of POM and Me-SATE deprotection can be tentatively explained, with reference to the two main structural features which induce the activity of mammalian esterases, i.e. the nature of the substrate functionality and the lipophilicity of the molecules. In this respect, polar or charged compounds are not the preferred substrate for these enzymes. Thus, one can hypothesize that the progressive carboxyesterase mediated deprotection of the gap decreases the affinity of the chimeric oligo as an enzyme substrate due to the successive increase in negative charge. Since phosphorodithioate oligos are more lipophilic than phosphorothioate ones, and furthermore POM group is more lipophilic than Me-SATE group, we can assume that the change in lipophilicity of first oligonucleotide after the Me-SATE groups were removed, is not significant for the esterases. Furthermore we can exclude the possibility that one phosphorous configuration ($R_p$ or $S_p$) is a better substrate than the other as we did not find any difference of the hydrolysis rate for the both diastereoisomers of the POM dithymidine phosphorothioate triester [Tp(POM)T] and for the both diastereoisomers of the tetrathymidine bearing a central POM phosphrothioate triester [Tp(POM)Tp(O⁻)T] in total CEM cell extract. In the case of second oligonucleotide, the half-life is long enough to allow concomitant nucleophilic attack by chemical nucleophiles present in the medium. However such nucleophilic attack, if any, should mainly occur on the carbonyl function instead of on the phosphorous atom since we did not observe any formation of PO bound formation on HPLC profiles.

EXAMPLE 13
Synthesis of oligonucleotide having mixed sequences and S-pivaloyl thioethyl blocking groups Oligonucleotides are synthesized via the procedure of Example 1 using the nucleotide amidites of Examples 7 through 10. After the precipitation step, the mixed sequences oligonucleotides having the blocking groups of the invention can be used in vivo in the normal manner.

EXAMPLE 14
1-o-Nitrophenyl-3-butenol, IV-2

The title compound was obtained from 2-nitrobenzaldehyde (1) (550.4 mg, 3.6 mmol) in dry dichloromethane by addition of titanium tetrachloride in methylene chloride (1.0M, 8.7 ml), followed by the addition of allyltrimethylsilane (2.1 ml, 13 mmol) with 83% yield as described by Ordoukhanian, et al., *J. Am. Chem Soc.* 1995, 117, 9570–9571. ¹H-NMR (250 MHz, CDCl₃/TMS) δ 7.92 (dd, 1H), 7.82 (dd, 1H), 7.64 (td, 1H), 7.41 (td, 1H), 7.24 (s, CDCl₃), 5.88 (m, 1H), 5.31 (dd, 1H), 5.20 (m, 2H), 2.7 (m, 1H), 2.41 (m, 2H).

EXAMPLE 15
1-o-Nitrophenyl-1-O-dimethoxytrityl-3-ene-1-butenol, IV-3

To a stirring solution of the alcohol 2 (564.2 mg, 2.94 mmol) in dry pyridine (30 ml) at 0° C. was added triethylamine (590 µl, 4.23 mmol) and 4-(dimethyl amino) pyridine (15.8 mg, 0.13 mmol). The mixture was stirred for 15 min prior to the addition of 4,4'-dimethoxytritylchloride (3.5 g, 10.38 mmol). The mixture was then allowed to stir 2 days warming to room temperature in the process. The solvent was removed under reduced pressure, and the resulting residue was dissolved in ethyl acetate and extracted with a saturated solution of sodium bicarbonate. The aqueous layer was further extracted with ethyl acetate and the organic layers combined and dried with sodium sulfate, and the solvent was removed under reduced pressure. The resulting residue was chromatographed on a silica gel column (2% ethyl acetate/2% triethylamine/hexane) to give the desired dimethoxytrityl alcohol (1.1 g, 2.22 mmol) as a yellow-orange oil in 65% yield. ¹H-NMR (250 MHz, CDCl₃/TMS) δ 7.65 (m, 2H), 7.51 (m, 2H), 7.38–7.09 (m, 9H), 6.66 (m, 4H), 5.95 (m, 1H), 5.42 (dd, 1H), 5.00 (m, 2H), 3.77 (d, 6H), 2.79 (m, 1H), 2.61 (m, 1H).

EXAMPLE 16
1-o-Nitrophenyl-1-O-dimethoxytrityl-1,3-propanediol, IV-6

Osmium tetroxide (143 µl, 55 mM in water) was added to a solution of dimethoxytrityl alcohol 3 (788.1 mg, 1.59 mmol) in dioxane/water (18 ml, 5:1 v:v) followed by the addition of sodium periodate (855.4 mg, 3.98 mmol). The mixture was stirred at room temperature for 9 hours. The mixture was cooled at 0° C. and sodium borohydride (150.6 mg, 3.98 mmol) was added to the mixture. Then, it was allowed to warm to room temperature and stirred for an additional 40 min. The mixture was cooled at 0° C. and the excess of sodium borohydride was quenched with acetone (4 ml). After the extraction with dichloromethane (50 ml), the organic layer was washed with a saturated solution of sodium bicarbonate (50 ml). The aqueous layer was extracted with dichloromethane (50 ml) and the organic layers combined and dried with dry sodium sulfate. Removal of the solvent under reduced pressure gave a residue which was chromatographed on a silica gel column (30% dichloromethane/1% triethylamine/hexane). The yellow oil obtained (372.1 mg, 0.74 mmol) was the desired compound IV-6 in 47k yield. $^1$H-NMR (250 MHZ, CDCl$_3$/TMS) δ 7.73 (m, 2H), 7.44 (m, 2H), 7.32–7.13 (m-9H), 6.69 (M, 4H), 5.52 (dd, 1H), 3.75 (m, 8H), 2.37 (m, 1H), 1.65 (bs, 1H).

EXAMPLE 17

1-o-Nitrophenyl-1-O-dimethoxytrityl-3-O-[N.N-diisopropylamine-O-cyanoethyl phosphine]-1,3-propanediol, IV-7

To a stirring solution of the diol IV-6 (1.4 g, 2.80 mmol) in dry dichloromethane (12 ml) was added tetrazolure of diisopropylammonium (242.3 mg, 1.4 mmol) followed by the addition of bis-(diisopropylamino)-O-cyanoethylphosphine (998 μl, 3.36 mmol). The mixture was stirred at room temperature and under argon for 3 hours. Then, the mixture was washed with a saturated solution of sodium bicarbonate and brine (50 ml). The aqueous layer was extracted with dichloromethane (50 ml) and the organic layers combined and dried with dry sodium sulfate. The solvent was removed under reduced pressure. The residue was dissolved in a minimum amount of toluene and the desired product IV-7 was isolated by precipitation at 78° C. into hexane (300 ml) in 75% yield. $^1$H-NMR (250 MHZ, CD$_3$CN/TMS) δ 7.62 (m, 2H), 7.45 (m, 2H), 7.36–7.08 (m, 9H), 6.63 (m, 4H), 5.36 (m, 1H), 3.75 (m, 10H), 3.53 (m, 2H), 2.56 (t, 2H), 2.34 (m, 2H), 1.30–1.05 (m, 12H). $^{31}$P-NMR (250 MHZ, CD$_3$CN/H$_3$PO$_4$) δ 147.56, 147.45.

EXAMPLE 18

Spacer incorporation (via phosphoramidate linkage formation).

The incorporation of the spacer on commercial Long Chain Alkylamine Control Pore Glass (500 A from Aldrich, 392 mg) was carried out on a 10 μmole scale on a DNA synthesizer/Applied Biosystem Inc., 381 A). The coupling reaction was effected by 0.2 M solution of phosphoramidite IV-7 and 0.05 M tetrazole in acetonitrile over a period of 3 min. The capping reaction was performed with conventional commercial reagents over a period of 5 min. The oxidation reaction was effected by the commercially available iodine/water/pyridine mixture in 1 min. The spacer loading averaged about 70 μmoles/gram as determined by absorbance of dimethoxytrityl cation.

EXAMPLE 19

Photolysis deprotection

Photolysis was carried using a high-pressure Hg lamp, with a pyrex filter. The cuve (quartz) containing the support was thermostated (room temperature). The support in suspension into acetonitrile/water (9:1) was irradiated by UV light above 280 nm. After 10–20 min of irradiation, the photolabile linker was cleaved and then the triester oligonucleotide liberated. The yield of photolysis reaction was 70–80%

EXAMPLE 20

General Procedures For the Preparation of Phosphoramidites and Phosphoramidite Reagents A. Phosphoramidites (Way A)

Figure 6:
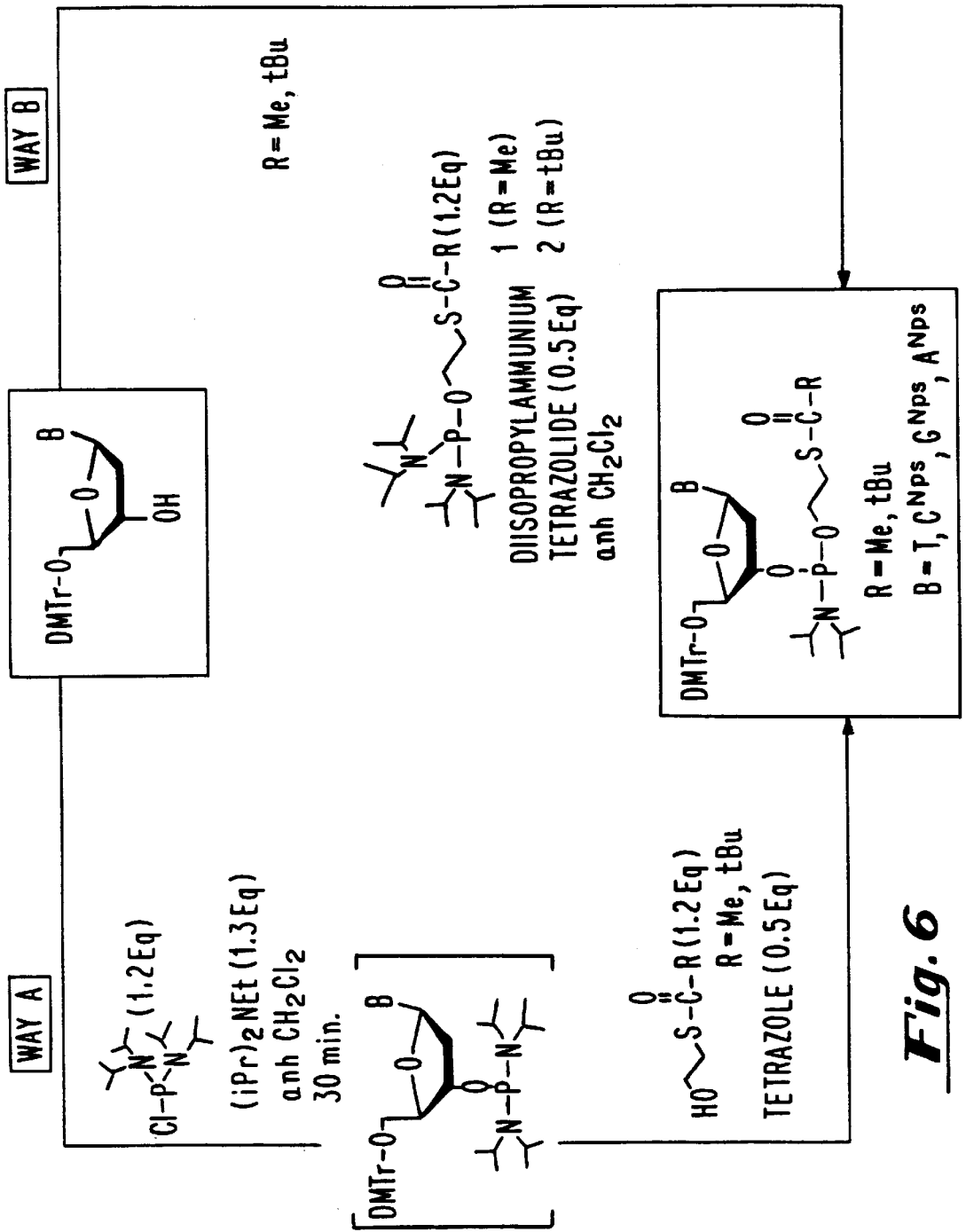
FIG. 6 shows synthetic routes to phosphoramidite reagents according to the invention.

Referring to FIG. 6, 5'-O-(4,4'-dimethoxytrityl) N-nitrophenylsulfenyl protected nucleosides were obtained as described by Chattopadhaya, *Acta Chemica Scandinavica B* 1983, 37, 857–864. To a cooled solution (ice bath) of 5'-O-(4,4'-dimethoxytrityl)-2'-deoxynucleoside (15.6 mmol) and diisopropylethylamine (3.3 mL, 20.3 mmol) in dry dichloromethane (100 mL) was added a solution of N,N-(diisopropylamino) chlorophosphine (5g, 18.7 mmol) in dry dichloromethane (18 mL). The resulting mixture was stirred at room temperature for 30 min. A solution of S-(2-hydroxyethyl) thioacetate (18.7 mmol) or S-(2-hydroxyethyl) thiopivaloate (10.2 mmol) and tetrazole (546.4 mg, 7.8 mmol) in dry dichloromethane (20 mL) was added dropwise and the stirring was maintained for 15 hours. After dilution with dichloromethane (200 mL), the mixture was washed with saturated hydrogenocarbonate (300 mL) and brine (2×300 mL), dried over sodium sulfate and evaporated under reduced pressure. The residue was purified by silica gel flash column chromatography and elution was performed using a stepwise gradient of ethyl acetate (10–40% in cyclohexane. After evaporation of the desired fractions, the residue was redissolved in benzene and lyophilized to give the corresponding phosphoramidite as a powder.

B=T, R=Me

68% yield; $^1$H-MNR (CD$_3$CN/TMS); δ (ppm); 9.23 (large s, 1H, NH base), 7.2–7.5 (m, 10H, aromatic H +H6), 6.85 (m, 4H, aromatic H), 6.24 (m, 1H, HI'), 4.6 (m, 1H, H3'), 4.07 (m, 1H, H4'), 3.74 (s, 6H, OCH$_3$), 3.55 (m, 4H, OCH$_2$ and CHN), 3.31 (M, 2H, H5' and H5"), 3.01 (m, 2H, CH$_2$CH$_2$S), 2.31 (m, 2H, H2' and H2"), 1.48 (m, 3H, CH$_3$dT), 1.13 (4d, 12H, CH(Me)$_2$), 1.05 (m, 3H, MeCO); $^{31}$P-MNR (CD$_3$CN/H$_3$PO$_4$); δ (ppm); 148.93, 148.54; FAB MS (<0,NOBA) m/z; 794 [M+H]+.

B=T, R=tBu

55% yield; $^1$H-NMR (CD$_3$CN/TMS); δ (ppm); 9.37 (large s, 1H, NH base), 7.2–7.6 (m, 10H, aromatic H +H6), 6.82 (m, 4H, aromatic H), 6.23 (m, 1H, H1'), 4.6 (m, 1H, H3'), 4.07 (m, 1H, H4'), 3.75 (s, 6H, OCH$_3$), 3.56 (m, 4H, OCH$_2$CH$_2$ and CHN), 3.31 (m, 2H, H5' and H5"), 2.97 (m, 2H, CH$_2$CH$_2$S), 2.36 (m, 2H, H2' and H2"), 1.48 (m, 3H, CH$_3$dT), 1.3 (4d, 12H, CH(Me)$_2$), 1.17 (3s, 9H, (Me)$_3$CCO); $^{31}$P-NMR (CD$_3$CN/H$_3$PO$_4$); δ (ppm); 149.22, 148.85; FAB MS (>0, GT) m/z; 834 [M+H]$^+$.

B=A$^{Nps}$, R=Me

60% yield; $^1$H-NMR (CD$_3$CN/TMS); δ (ppm); 8.28 (s, 1H, H2), 8.19 (s, 1H H8), 7.96 (large s, 1H, NH base), 7.42–7.33 (m, 3H, aromatic H from Nps protection) 7.23–7.21 (m, 9H, aromatic H), 6.76 (m, 4H, aromatic H), 6.39 (m, 1H, H1'), 4.88 (m, 1H, H3'), 4.19 (m, 1H, H4'), 3.71 (s, 6H, OCH$_3$), 3.55 (m, 4H, OCH$_2$CH$_2$ and CHN), 3.28 (m, 2H, H5' and H5"), 3.01 (m, 2H, CH$_2$CH$_2$S), 2.58 (m, 2H, H2' and H2"), 1.12 (4d, 12H, CH(Me)$_2$), 1.05 (m, 3H, MeCO); $^{31}$P-NMR (CD$_3$CN/H$_3$PO$_4$); δ (ppm); 149.44, 149.29; FAB MS (>0 G-T) m/z; 956 [M+H]+.

B=A$^{Nps}$, R=tBu

59% yield; $^1$HNMR (CD$_3$CN/TMS): δ (ppm): 8.27 (s, 1H, H2), 8.19 (s, 1H, H8), 7.97 (large s, 1H, NH base), 7.43–7.33 (m, 3H, aromatic H from Nps protection) 7.26–7.22 (m, 9H, aromatic H), 6.82 (m, 4H, aromatic H), 6.36 (m, 1H, H1'), 4.90 (m, H3'), 4.20 (m, 1H, H4'), 3.72 (s, 6H OCH$_3$), 3.53 (m, 4H, OCH$_2$CH$_2$ and CHN), 3.27 (m, 2H, H5' and H5"), 3.03 (m, 2H, CH$_2$CH$_2$S), 2.56 (m, 2H, H2' and H2"), 1.16

(3s, 9H, (Me)$_3$CCO), 1.13 (4d, 12 H, CH (Me)$_2$); 31P-NMR (CD$_3$CN/H$_3$PO$_4$): δ (ppm): 149.35; FAB MS (>0, G-T) m/z: 998 [M+H]$^+$.

B=C$^{Nps}$, R=Me

67% yield; $^1$H-NMR (CD$_3$CN/TMS) δ (ppm) 8.31 (d, 1H H6), 7.88–7.61 (m, 3H, aromatic H from Nps protection) 7.48–7.25 (m, 9H, aromatic H), 6.76 (m, 4H, aromatic H), 6.13 (m, 1H, H1'), 5.95 (d, 1H, H5), 4.57 (m, 1H, H3'), 4.06 (m, 1H, H4'), 3.71 (s, 6H, OCH$_3$), 3.59 (m, 4H, OCH$_2$CH$_2$ and CHN), 3.36 (m, 2H, H5' and H5"), 3.03 (m, 2H, CH$_2$Ch$_2$S), 2.98 (m, 2H, H2' and H2"), 1.18 (4d, 12H CH(Me)$_2$), 1.07 (m, 3H, MeCO); $^{31}$P-NMR (CD$_3$CN/ H$_3$PO$_4$): δ (ppm): 149.38; FAB MS (>0, G-T) m/z: 932 [M+H]$^+$.

B=C$^{Nps}$, R=tBu

64% Yield; $^1$H-NMR (CD$_3$CN/TMS); δ (ppm): 8.30(d, 1H, H6), 7.88–7.62 (m, 3H, aromatic H from Nps protection)7.49–7.25 (m, 9H, aromatic H), 6.75 (m, 4H, aromatic H), 6.14 (m, 1H, H1'), 5.96 (d, 1H, HS), 4.58 (m,1H, H3'), 4.06 (m, 1H, II4'), 3.70 (s, 6H, OCH$_3$), 3.60 (m, 4H, OCH$_2$CH$_2$ and CHN), 3.35 (m, 2H, H5' and H5"), 3.01 (m, 2H, CH$_2$CH$_2$S), 2.97 (m, 2H, H2' and H2"), 1.19 (3s, 9H, (Me)$_3$CCO), 1.16 (4d, 12H CH(Me)$_2$); $^{31}$P-NMR (CD$_3$CN/H$_3$PO$_4$); δ (ppm): 149.41; FAB MS (>0, G-T) m/z: 974 [M+H]$^+$.

B=G$^{Nps}$, R=Me

47% yield; $^1$H-NMR (CD$_3$CN/TMS): δ (ppm): 7.65 (s, 1H, H8), 8.19 (s, 1H, H8), 7.45–7.39 (m, 3H, aromatic H from Nps protection) 7.35–7.27 (m, 9H aromatic H), 6.75 (m, 4H, aromatic H), 6.09 (m, 1H, H1'), 4.47 (m, 1H, H3'), 4.11 (m, 1H, H4'), 3.69 (s, 6H, OCH$_3$), 3.56 (m, 4H, OCH$_2$CH$_2$ and CHN), 3.45 (m, 2H, H5' and H5"), 3.05 (m, 2H, CH$_2$CH$_3$S), 2.48 (m, 2H, H2' H2' and H2"), 1.16 (4d, 12H, CH(Me)$_2$), 1.03 (m, 3H, MeCO); $^{31}$P-NMR (CD$_3$CN/ H$_3$PO$_4$): δ (ppm): 149.8, 149.4; FAB MS (>0, G-T) m/z: 972[M+H]$^+$.

B=G$^{Nps}$, R=tBu

51% yield; $^1$H-NMR (CD$_3$CN/TMS): δ (ppm): 7.64 (s, 1H, H8), 8.17 (s, 1H, H8), 7.44–7.38 (m, 3H, aromatic H from Nps protection) 7.35–7.26 (m, 9II, aromatic H), 6.74 (m, 4H, aromatic H), 6.09 (m, 1H, H1'), 4.45 (m, 1H, H3'), 4.10 (m, 1H, H4'), 3.68 (s, 6H, OCH$_3$), 3.56 (m, 4H, OCH$_2$CH$_2$ and CHN), 3.46 (m, 2H, H5' and H5"), 3.06 (m, 2II, CH$_2$CH$_2$S), 2.47 (m, 2H, H2' and H2"), 1.17 (3s, 9H, (Me)$_3$CCO), 1.13 (4d, 12H, CH(Me)$_2$); $^{31}$P-NMR (CD$_3$CN/ H$_3$PO$_4$): δ (ppm) 149.56, 149.37; FAB MS (>0, G-T) m/z: I014[M+H]$^+$.

B. Phosphoramidites and Phosphoramidte Reagents (Way B)

1. Phosphoramidite Reagents

Referring to FIG. 6, a solution of S-(2-hydroxyethyl) thioacetate (10 mmol) or S-(2-hydroxyethyl) thiopivaloate (10 mmol) and thiethylamine (11 mmol) in diethyl ether (25 mL) was added dropwise to N,N-(diisopropylamino) chlorophosphine (10 mmol) in diethyl ether (25 mL) under argon at 0° C. The reaction mixture was stirred at room temperature for 2 h, after which the resulting triethylammonium hydrochloride was filtered off. Cyclohexane (50 mL) was added and the mixture was evaporated under reduced pressure to give a pale yellow oil. Purification by flash column chromatography gave the title compounds 1 and 2 as colorless oils.

(S-acetyl-2-thioethyl) bis [N,N-diisopropylphosphoramidite] (1): 70% yield, after flash column chromatography [eluent, stepwise gradient of ethyl acetate (0–10%) in cyclohexane containing 1% triethylamine]; $^1$H NMR (DMSO-d$_6$) δ 3.6 (m, 2H, CH$_2$CH$_2$O), 3.47 (m, 4H, Me$_2$CHN, 3.04 (t, 2H, SCH$_2$CH$_2$), 2.34 (s, 3H, MeCO), 1.10 (m, 24H, Me$_2$CHN); $^{31}$ P NMR (DMSO-d$_6$) δ 125.3 (s); FAB MS (>0, G-T) m/e: 351 [M+H]$^+$.

(S-pivaloyl-2-thioethyl) bis [N,N-diisopropylphosphoramidite] (2): 90% yield, after flash column chromatography [eluent, stepwise gradient of ethyl acetate (0–5%) in cyclohexane containing 1% triethylamine]; $^1$H NMR (MSO-d$_6$) δ 3.56 (m,2H, CH$_2$CH$_2$O), 3.47 (m, 4H, Me$_2$ CHN), 3.01 (t, 2H, CH$_2$CH$_2$), 1.16 (s, 9H, tBuCO), 1.10 (m, 24H, Me$_2$CHN); $^{31}$P NMR (DMSO-d$_6$) δ 124.6 (s); FAB MS (>0, NBA) m/c: 411 [M+O+H]$^+$, FAB MS (>0, G-T) m/e: 393 [M+H]$^+$.

2. Phosphoramidites (NPS or PNT Protocol)

5'-O-(4,4'-dimethoxytrityl)-2'-deoxynucleoside (1 mmol; B=T, A$^{Nps}$, C$^{nps}$, G$^{nps}$) was dissolved in dry acetonitrile (5 mL), evaporated to dryness and then redissolved in dry dichloromethane (5 mL). Diisopropylammonium tetrazolide (0.5 mmol) and phosphoramidite 1 or 2 (1.2 mmol) were added to this solution and the reaction mixture was stirred for 4 h at room temperature. After taking up in ethyl acetate (40 mL), the mixture was washed with a saturated solution of sodium bicarbonate (40 mL) and brine (40 mL). The organic layer was dried over sodium sulfate and concentrated in vacuo. The crude was purified by silica gel flash column chromatography, 55% to 70% [eluent, stepwise gradient of ethyl acetate in cyclohexane]. $^1$H-$^{31}$P-NMR data are listed above.

5'-O-(4,4,-Dimethoxytrityl) N-Pent-4-enoyl protected nucleosides were obtained as described by S Agrawal in Journal Of Organic Chemistry (1995).

B=A$^{PNT}$,R=tBu

59% yield, $^1$H-NMR (CDCl$_3$/TMS):δ (ppm): 8.64 (s, 1H, H2), 8.52 (large s, 1H, NH base), 8.18 (s, 1H, H8), 7.43–7.23 (m, 9H, aromatic H), 6.8 (m, 4H aromatic H), 6.49 (m, 1H, H1'), 5.94 (m, 1H, CH=CH$_2$-PNT), 5.21 (m, 2H, CH=CH$_2$-PNT), 4.78 (m, 1H, H3,), 4.35 (m, 1H, H4,), 3.81 (s, 6H, OCH$_3$), 3.62 (m, 4H, OCH$_2$CH$_2$ and CHN), 3.4 (m, 2H,H5, and H5"), 3.05 (m, 4H, CH$_2$CH$_2$S and COCH$_2$CH$_2$-PNT), 2.98–2.72 (m, 2H, H2' and H2") 2.56 (m, 2H, COCH$_2$CH$_2$-PNT), 1.27 (3s, 9H, (Me)$_3$CCO), 1.21 (4d 12H, CH(Me) $_2$), $^{31}$P-NMR (CDC$_3$/H$_3$/PO$_4$): δ (ppm): 149.06–148.99, FAB MS (>0, NBA) m/z: 927 [M+H]$^+$.

B=C$^{PNT}$, R=tBu

64% yield, $^1$H-NMR (CDCl$_3$/TMS):δ (ppm): 8.24 (d, 1H, H6), 7.38–7.20 (m, 9H, aromatic H), 7.05 (d, 1H, H5), 6.8 (m, 4H aromatic H), 6.22 (m, 1H, H1'), 5.78 (m, 1H, CH=CH$_2$-PNT), 5.04 (m, 2H, CH=CH$_2$-PNT), 4.56 (m, 1H, H3,), 4.17 (m, 1H, H4,), 3.76 (s, 6H, OCH$_3$), 3.55 (m, 4H, OCH$_2$CH$_2$ and CHN), 3.37 (m, 2H,H5, and H5"), 2.96 (m, 2H, CH$_2$CH$_2$S), 2.70(m, 1H, H2' and H2") 2.50–2.36 (m, 4H, COCH$_2$CH$_2$-PNT), 2.22 (m, 1H, H2"),1.14 3s,9H, (Me)$_3$CCO) 1.06 (4d, 12H, CH(Me)$_2$),$^{31}$P-NMR (CDCl$_3$/ H$_3$/PO$_4$): δ (ppm): 148.9–148.3, FAB MS (>0, NBA) m/z: 903 [M+H]$^+$.

EXAMPLE 21

Synthesis of Dodecathymidine SATE (R=Me) and tBuSATE (R=tBu) Phosphodiesters (X=0) and Phosphorothionotriesters (X=S).

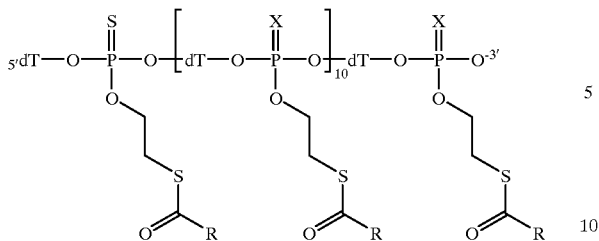

The automated solid-phase synthesis of the modified oligonucleotides was carried out on a 10 μmole scale on a DNA synthesizer (Applied Biosystems Inc., 381A) using phosphoramidite chemistry. The first, second, and third coupling reactions were performed by 0.1 M solutions of phosphoramidites (R=Me or tBu) and 0.5 M tetrazole over a period of 4 min and of 1.5 min for the following coupling steps. The oxidation reaction required for the preparation of oligodeoxyribonucleoside phosphotrieters (X=O) was effected by a 1.1 M solution of ter-butyl hydroperoxide in toluene/dichloromethane (3.6/6.4, v/v) over a period of 1.8 min. The oxidative sulfurization reaction required for the preparation of oligodeoxyribonucleoside phosphorothionotriesters (X=S) was effected by a 0.05 M solution of crystalline 3H-1,2-benzodithiole-3-one-1,1-dioxide ("Beaucage reagent") in acetonitrile. The sulfurization reaction was performed over a period of 1.4 min. In order to obtain a phosphorothioate triester linkage at the 5'-end of the oligonucleotides (last incorporation), the oxidative sulfurization was performed with the Beaucage reagent as previously described or with a treatment with a 5% solution of elemental sulfur in carbon disulfide/pyridine (1/1, v/v) during 8 min.

Following the 10 μmole synthesis, a third of the controlled pore glass solid support was flushed with argon then irradiated with UV light (>280 nm, pyrex filter) at room temperature during 20 min. The suspension was filtered and the resulting solution was evaporated. The residue was redissolved in a dioxane/water solution (5/3, v/v) and lyophilized to give the oligonucleotides as white powders. The two other thirds of the solid support were treated as the first one.

X=O,R-Me
Yield 26.7 mg,
$^{31}$P NMR (dioxane/D$_2$O): δ (ppm) 68 (1P), 0.3 (1P), −1.09 (10P)
MS MALDI-TOF: calc mass 4910.32, exp. mass 4907.1
X=S,R=Me
Yield 27.5 mg,
$^{31}$P NMR (dioxane/D$_2$O): δ (ppm) 68 (11), 57.3 (1P)
MS MALDI-TOF: calc mass 5087.03, exp. mass 5090.7
X=O,R=tBu
Yield 43 mg,
$^{31}$P NMR (dioxane/D$_2$O): δ (ppm) 68.2 (1P), 0.14 (1P), −0.78 (10P)
MS MALDI-TOF: calc mass 5415.29, exp. mass 5417.8
X=O,R=tBu
Yield 35.1 mg,
$^{31}$P NMR (dioxane/D$_2$O): δ (ppm) 68.4 (11P),57.5 (1P)
MS MALDI-TOF: calc mass 5592, exp. mass 5587.3

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry or related fields are intended to be within the scope of the following claims.

What is claimed is:

1. A compound of the structure:

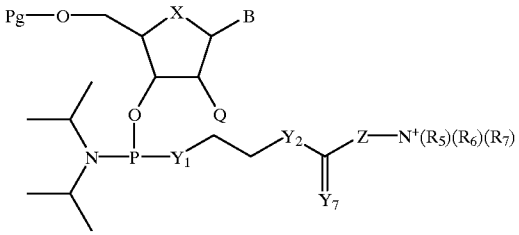

wherein
Pg is a nucleoside blocking group,
B is a heterocyclic base,
$Y_1$ is S and $Y_2$ is O or S or $Y_1$ is O and $Y_2$ is S,
Q is F or O-alkyl,
Z is hydrocarbyl,
X is O, S, or CH$_2$,
$Y_7$ is O or S, and
$R_5$, $R_6$, and $R_7$ are, independently, hydrocarbyl.

2. The compound of claim 1 wherein Z is $C_1$–$C_4$ alkyl.
3. The compound of claim 1 wherein Z is t-butyl.
4. The compound of claim 1 wherein Z in methyl.
5. The compound of claim 1 wherein said hydrocarbyl group is substituted with at least one of a halogen, hydroxyl, thiol, keto, carboxyl, trifluoromethyl, trifluoromethoxy, O-alkyl, S-alkyl, NH-alkyl, N-dialkyl, O-aralkyl, S-aralkyl, NH-aralkyl, amino, or nitro group.
6. The compound of claim 1 wherein $R_5$, $R_6$, and $R_7$ are, independently, $C_1$–$C_{20}$ alkyl.
7. The compound of claim 1 wherein $R_5$, $R_6$, and $R_7$ are, independently, $C_1$–$C_4$ alkyl.
8. The compound of claim 1 wherein $R_5$, $R_6$, and $R_7$ are methyl.
9. The compound of claim 1 wherein B is a purine or pyrimidine.
10. The compound of claim 9 wherein an exocyclic nitrogen atom of said purine or pyrimidine further includes a base-stable protecting group.
11. The compound of claim 10 wherein said purine or pyrimidine is adenine, guanine, or cytosine.
12. The compound of claim 10 wherein said protecting group is selected from the group consisting of pent-4-enoyl, 4-methylsulphinyl-benzyloxycarbonyl, 2-nitrophenylsulfenyl, and triphenyl-methanesulfenyl.
13. The compound of claim 1 wherein Pg is trityl, monomethoxytrityl, dimethoxytrityl or pixyl.
14. The compound of claim 1 wherein Pg is dimethoxytrityl.
15. The compound of claim 1 wherein $Y_2$ is S.
16. The compound of claim 1 wherein Q is O—$C_1$—$C_{20}$ alkyl.
17. The compound of claim 16 wherein said alkyl group is substituted with at least one of a halogen, hydroxyl, thiol, keto, carboxyl, trifluoromethyl, trifluoromethoxy, O-alkyl, S-alkyl, NH-alkyl, N-dialkyl, O-aralkyl, S-aralkyl, NH-aralkyl, amino, or nitro group.
18. The compound of claim 1 wherein Q is F.

19. A compound of the structure:

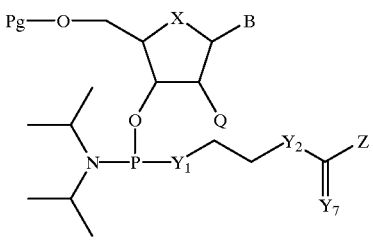

wherein
Pg is a nucleoside blocking group,
B is a heterocyclic base,
$Y_1$ is S and $Y_2$ is O or S or $Y_1$ is O and $Y_2$ is S,
Q is F or O-alkyl,
Z is hydrocarbyl,
X is O, S, or $CH_2$, and
$Y_7$ is O or S.

20. The compound of claim 19 wherein Z is $C_1$–$C_4$ alkyl.
21. The compound of claim 19 wherein Z is t-butyl.
22. The compound of claim 19 wherein Z in methyl.
23. The compound of claim 19 wherein said hydrocarbyl group is substituted with at least one of a halogen, hydroxyl, thiol, keto, carboxyl, trifluoromethyl, trifluoromethoxy, O-alkyl, S-alkyl, NH-alkyl, N-dialkyl, O-aralkyl, S-aralkyl, NH-aralkyl, amino, or nitro group.
24. The compound of claim 19 wherein B is a purine or pyrimidine.
25. The compound of claim 24 wherein an exocyclic nitrogen atom of said purine or pyrimidine further includes a base-stable protecting group.
26. The compound of claim 25 wherein said purine or pyrimidine is adenine, guanine, or cytosine.
27. The compound of claim 25 wherein said protecting group is selected from the group consisting of pent-4-enoyl, 4-methylsulphinyl-benzyloxycarbonyl, 2-nitrophenylsulfenyl, and triphenyl-methanesulfenyl.
28. The compound of claim 19 wherein Pg is trityl, monomethoxytrityl, dimethoxytrityl or pixyl.
29. The compound of claim 19 wherein Pg is dimethoxytrityl.
30. The compound of claim 19 wherein $Y_2$ is S.
31. The compound of claim 19 wherein Q is O—$C_1$–$C_{20}$ alkyl.
32. The compound of claim 31 wherein said alkyl group is substituted with at least one of a halogen, hydroxyl, thiol, keto, carboxyl, trifluoromethyl, trifluoromethoxy, O-alkyl, S-alkyl, NH-alkyl, N-dialkyl, O-aralkyl, S-aralkyl, NH-aralkyl, amino, or nitro group.
33. The compound of claim 19 wherein Q is F.
34. A compound of the structure

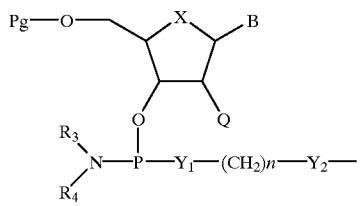

wherein:
Pg is a nucleoside blocking group,
B is a heterocyclic base,
$Y_1$ is S and $Y_2$ is O or S or $Y_1$ is O and $Y_2$ is S,
$R_3$ and $R_4$, independently, are hydrocarbyl or together $R_3$ and $R_4$ are part of a nitrogen heterocyclic ring,
Q is F or O-alkyl,
n is 1 to 6,
said $Y_2$ is covalently bound to S-Z, C(=$Y_7$)—Z, or C(=$Y_7$)—Z—$N^+(R_5)$ $(R_6)$ $(R_7)$,
Z is hydrocarbyl,
X is O, S, or $CH_2$,
$Y_7$ is O or S, and
$R_5$, $R_6$, and $R_7$ are, independently, hydrocarbyl.

35. The compound of claim 34 wherein $Y_2$ is covalently bound to —C(=$Y_7$)—Z.
36. The compound of claim 34 wherein $Y_2$ is covalently bound to —S—Z.
37. The oligonucleotide of claim 34 wherein $Y_2$ is covalently bound to —C(=$Y_7$)—Z—$N(R_5)$ $(R_6)$ $(R_7)$.
38. The compound of claim 34 wherein n is 2.
39. The compound of claim 34 wherein Z is $C_1$–$C_{20}$ alkyl.
40. The compound of claim 35 wherein Z is $C_1$–$C_{20}$ alkyl.
41. The compound of claim 34 wherein Z is $C_1$–$C_4$ alkyl.
42. The compound of claim 35 wherein Z is $C_1$–$C_4$ alkyl.
43. The compound of claim 35 wherein Z is i-propyl or t-butyl.
44. The compound of claim 35 wherein Z in methyl.
45. The compound of claim 34 wherein said hydrocarbyl group is substituted with at least one of a halogen, hydroxyl, thiol, keto, carboxyl, trifluoromethyl, trifluoromethoxy, O-alkyl, S-alkyl, NH-alkyl, N-dialkyl, O-aralkyl, S-aralkyl, NH-aralkyl, amino, or nitro group.
46. The compound of claim 37 wherein $R_5$, $R_6$, and $R_7$ are, independently, $C_1$–$C_{20}$ alkyl.
47. The compound of claim 37 wherein $R_5$, $R_6$, and $R_7$ are, independently, $C_1$–$C_4$ alkyl.
48. The compound of claim 37 wherein $R_5$, $R_6$, and $R_7$ are methyl.
49. The compound of claim 34 wherein B is a purine or pyrimidine.
50. The compound of claim 49 wherein said purine or pyrimidine includes an exocyclic amine bearing a base-stable protecting group.
51. The compound of claim 50 wherein said purine or pyrimidine is adenine, guanine, or cytosine.
52. The compound of claim 50 wherein said protecting group is selected from the group consisting of pent-4-enoyl, 4-methylsulphinyl-benzyloxycarbonyl, 2-nitrophenylsulfenyl, and triphenyl-methanesulfenyl.
53. The compound of claim 34 wherein Pg is trityl, monomethoxytrityl, dimethoxytrityl or pixyl.
54. The compound of claim 53 wherein Pg is dimethoxytrityl.
55. The compound of claim 34 wherein each of $R_3$ and $R_4$ are $C_1$–$C_{10}$ alkyl.
56. The compound of claim 34 wherein each of $R_3$ and $R_4$ are iso-propyl.
57. The compound of claim 34 wherein $Y_1$ is O and $Y_2$ is S.
58. The compound of claim 34 wherein $Y_1$ is S and $Y_2$ is O.
59. The compound of claim 34 wherein $Y_1$ is S and $Y_2$ is S.
60. The compound of claim 34 wherein Q is O—$C_1$–$C_{20}$ alkyl.
61. The compound of claim 60 wherein said alkyl group is substituted with at least one of a halogen, hydroxyl, thiol, keto, carboxyl, trifluoromethyl, trifluoromethoxy, O-alkyl, S-alkyl, NH-alkyl, N-dialkyl, O-aralkyl, S-aralkyl, NH-aralkyl, amino, or nitro group.

62. The compound of claim 34 wherein Q is F.

* * * * *